(12) United States Patent
Charman et al.

(10) Patent No.: US 7,128,922 B1
(45) Date of Patent: Oct. 31, 2006

(54) COMPOSITIONS OF LEUKAEMIA INHIBITORY FACTOR

(75) Inventors: Susan Ann Charman, Brighton (AU); Anthony John Radford, Kew (AU)

(73) Assignee: Amrad Operations Pty Ltd, Victoria (AU)

( * ) Notice: Subject to any disclaimer, the term of this patent is extended or adjusted under 35 U.S.C. 154(b) by 0 days.

(21) Appl. No.: 09/555,108

(22) PCT Filed: Nov. 26, 1998

(86) PCT No.: PCT/AU98/00981

§ 371 (c)(1),
(2), (4) Date: Jul. 21, 2000

(87) PCT Pub. No.: WO99/27950

PCT Pub. Date: Jun. 10, 1999

(30) Foreign Application Priority Data

Nov. 26, 1997 (AU) .................................. PP0531

(51) Int. Cl.
*A61K 9/00* (2006.01)
*A61K 45/00* (2006.01)
*A61K 38/16* (2006.01)
*A61K 38/00* (2006.01)

(52) U.S. Cl. .................... 424/400; 424/85.2; 514/8; 514/21

(58) Field of Classification Search .............. 530/350, 530/351; 514/2, 12, 21, 970, 8; 424/400, 424/85.2
See application file for complete search history.

(56) References Cited

U.S. PATENT DOCUMENTS

| 5,187,077 A | 2/1993 | Gearing et al. |
| 5,418,159 A | 5/1995 | Gough et al. |
| 5,427,925 A | 6/1995 | Gearing et al. |
| 5,443,825 A | 8/1995 | Gearing et al. |
| 5,641,676 A | 6/1997 | Gough et al. |
| 5,750,654 A | 5/1998 | Gearing et al. |
| 5,824,838 A | 10/1998 | Melmed et al. |
| 5,962,321 A | 10/1999 | Gough et al. |
| 6,156,729 A * | 12/2000 | Patterson et al. |

OTHER PUBLICATIONS

Cleland, J. L. et al. The development of stable protein formulations: a close look at protein aggregation, deamidatin, and oxidation. Critical Reviews in Therapeutic Drug Carrier Systems 10(4): 307-377, 1993.*
Abstract of Van Vlasselaer et al, Prog Growth Factor Res, 1992, vol. 4, pp. 337-353.*
Abstract of Taupin et al, Int Rev Immunol, 1998, vol. 16, pp. 397-426.*
Abstract of Hilton et al, Journal of Cell Biochemistry, 1991, vol. 46, pp. 21-26.*

* cited by examiner

*Primary Examiner*—Karen A. Canella
(74) *Attorney, Agent, or Firm*—Scully, Scott, Murphy & Presser

(57) ABSTRACT

The present invention relates generally to compositions and more particularly to compositions comprising leukaemia inhibitory factor (hereinafter referred to as "LIF") or derivative or homologues thereof. The compositions of the present invention are particularly useful as compositions which exhibit enhanced stability and/or which exhibit reduced aggregation and/or reduced deamidation of LIF, its derivatives or other active ingredients.

49 Claims, 7 Drawing Sheets

Time (min)
Representative Reversed Phase Chromatogram
for LIF 1.0 mg/ml Standard Solution Representative Ion Exchange Chromatogram
for LIF 1.0 mg/ml Standard Solution Representative Size Exclusion Chromatogram for LIF 1.0 mg/ml Standard Solution Individual Freeze/Thaw Cycling Results Individual Freeze/Thaw Cycling Results Individual Freeze/Thaw Cycling Results Individual Freeze/Thaw Cycling Results Individual Freeze/Thaw Cycling Results

COMPOSITIONS OF LEUKAEMIA INHIBITORY FACTOR

FIELD OF THE INVENTION

The present invention relates generally to compositions and more particularly to compositions comprising leukaemia inhibitory factor (hereinafter referred to as "LIF") or derivative or homologues thereof. The compositions of the present invention are particularly useful as compositions which exhibit enhanced stability and/or which exhibit reduced aggregation and/or reduced deamidation of LIF, its derivatives or other active ingredients.

BACKGROUND OF THE INVENTION

LIF is a polyfunctional glycoprotein with diverse actions on a broad range of tissue and cell types, including induction of differentiation in a number of myeloid leukaemic cell lines, suppression of differentiation in normal embryonic stem cells, stimulation of proliferation of osteoblasts and DA-1 haemopoietic cells and potentiation of the of the proliferative action of interleukin-3 (IL-3) on megakaryocyte precursors. Functionally, LIF is able to switch autonomic nerve signalling from adrenergic to cholinergic mode, stimulate calcium release from bones, stimulate the production of acute phase proteins by hepatocytes and induce loss of fat deposits by inhibiting lipoprotein lipase-mediated lipid transport into adipocytes.

With a potentially broad range of clinical applications, it is imperative that compositions containing LIF are presented in a stable form and remain so during an extended period which may include shipment, handling and storage. Thus, a stable composition is one which retains its physical, chemical, therapeutic and toxicological profile over this period.

Deamidation is the most significant chemical degradation of LIF over time. It is clearly desirable that this process is minimized. Adsorption of LIF onto surfaces of containers, vials, syringes and infusion tubing is also a potential problem and must be minimized to ensure accurate dose and concentration. Physical degradation, such as aggregation or flocculation, may occur due to denaturation caused by elevated temperatures and/or agitation and excessive handling of the composition. Such degradation is clearly undesirable in terms of appearance and more importantly, consistent and effective administration of LIF in clinical applications. Storage at temperatures below room temperature typically retards chemical degradation, with storage in the frozen state being generally the most effective. Whilst this may minimize chemical degradation, the process of thawing the composition may then result in aggregation.

Thus, there exists a need for a stable composition and, in particular, a stable pharmaceutical composition of LIF and/or its derivatives or homologues wherein chemical and physical degradation is minimised.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention contemplates a composition comprising leukaemia inhibitory factor (LIF) or a derivative or homologue thereof and a stabilizing agent facilitating chemical and/or physical stability of LIF in the composition, additives for maintaining pH and isotonicity and one or more pharmaceutically acceptable carriers and/or diluents.

Another aspect of the invention provides a composition with improved chemical and physical stability comprising LIF or a derivative or homologue thereof, a stabilizing agent, additives for maintaining pH and isotonicity and one or more pharmaceutically acceptable carriers or diluents under conditions in which aggregation of LIF is reduced.

Yet another aspect of the invention provides a composition with improved chemical and physical stability comprising LIF or a derivative or homologue thereof, a stabilizing agent, additives for maintaining pH and isotonicity and one or more pharmaceutically acceptable carriers or diluents under conditions in which deamidation of LIF is reduced.

Still another aspect the present invention is directed to a stable composition comprising LIF or a derivative or homologue thereof, together with one or more pharmaceutically acceptable carriers or diluents, wherein the composition has a pH of between about 3.5 and about 6.5.

A further aspect the present invention provides a stable composition comprising LIF or a derivative or homologue thereof, together with one or more pharmaceutically acceptable carriers or diluents, wherein the composition has a pH of between about 3.5 and about 6.5 under conditions in which aggregation of LIF is reduced.

Another aspect the present invention contemplates a stable composition comprising LIF or a derivative or homologue thereof, together with one or more pharmaceutically acceptable carriers or diluents, wherein the composition has a pH of between about 3.5 and about 6.5 under conditions in which deamidation of LIF is reduced.

Yet another aspect of the present invention contemplates a method for preparing a composition comprising Leukaemia Inhibition Factor (LIF) or a derivative or homologue thereof and which exhibits reduced deamidation and/or aggregation of LIF or a derivative or homologue over time said method comprising admixing LIF or its derivative or homologue with a stabilizing agent.

Still another aspect of the present invention is directed to the use of a stabilizing agent in the manufacture of a composition exhibiting improved chemical and/or physical stability of Leukaemic Inhibitory Factor (LIF) or a derivative or homologue thereof.

Preferred compositions in accordance with the present invention are referred to as "pharmaceutical compositions" where LIF or its derivatives or homologues is/are present in a pharmaceutically acceptable composition.

DESCRIPTION OF THE PREFERRED EMBODIMENTS

Figure 1:
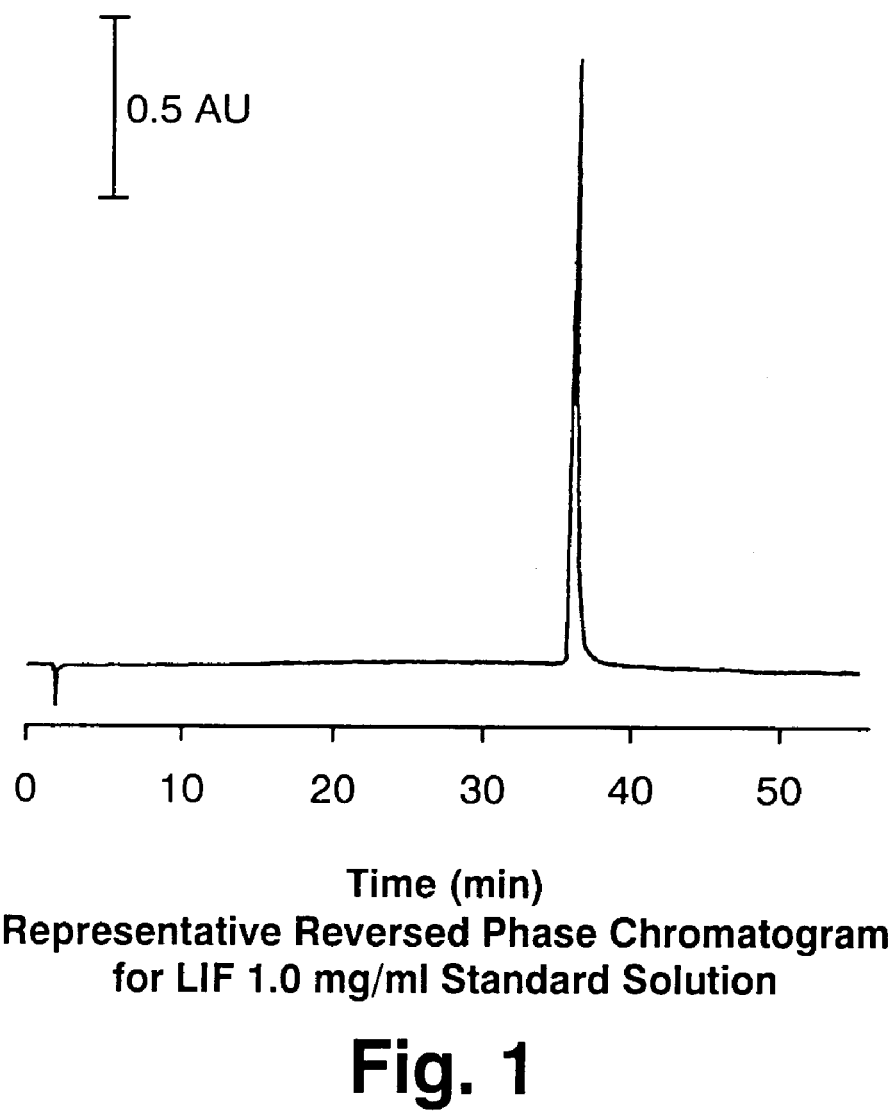
FIGS. 1 to 3, respectively, are a diagrammatic representations of Reversed Phase, Ion Exchange and Size Exclusion chromatograms for a 1.0 mg/ml standard solution of LIF prepared as described in Example 1 by diluting "stock" solution with 2 mM phosphate buffer, pH 6.42, containing 0.01% polysorbate.

The present invention provides compositions comprising LIF or its derivatives or homologues. The present invention particularly provides LIF or related molecules in a stable form.

Unless otherwise specified, the term "LIF" or "Leukaemia Inhibitory Factor" refers herein to synthetic, recombinant or purified naturally occurring LIF from animal or avian species. Preferred animal species are mammals such as humans, primates and livestock animals as well as any or all derivatives or homologues of LIF (e.g. sheep, pigs, cows, goats, donkeys and horses), laboratory animals (e.g. murine species, guinea pigs, rabbits and hamsters), companion animals (e.g. dogs and cats) or captive wild animals (e.g. kangaroos, foxes, and deer). Preferred avian species include but are not limited to caged birds, chickens, ducks, geese and game birds. As referred to here, LIF or Leukaemia Inhibitory Factor includes reference to derivatives, homologues and analogues of LIF. Derivatives, homologues, mimetics and analogues include parts, fragments or portions of LIF which are functionally active or which otherwise have a useful biological activity (eg. as an antagonist, antigen to induce antibody formation, as a diagnostic agent or as a therapeutic molecule). Such derivatives or parts thereof include any one or more contiguous series of amino acids contained within any one of the above LIF molecules and includes single or multiple amino acids substitutions, deletions and/or additions to or in the natural, synthetic or recombinant LIF molecule as well as hyperglycosolated and deglycosolated forms. Conditions for preparing recombinant LIF are disclosed in International Patent Application Nos PCT/AU88/00093 and PCT/AU90/00001 although these conditions may vary depending on the host cell used. Any such variations and/or modifications are within the scope of the subject invention. The host cells may be eukaryotic (eg. yeast, mammalian, insect, plant etc) or prokaryotic (eg. *Escherichia coli*, *Bacillus* sp, *Pseudomonas* sp etc) cells.

Accordingly, one aspect of the present invention contemplates a composition comprising leukaemia inhibitory factor (LIF) or a derivative or homologue thereof and a stabilizing agent facilitating chemical and/or physical stability of LIF in the composition, additives for maintaining pH and isotonicity and one or more pharmaceutically acceptable carriers and/or diluents.

Another aspect of the present invention provides a composition with improved chemical and physical stability comprising LIF or a derivative or homologue thereof, a stabilizing agent, additives for maintaining pH and isotonicity and one or more pharmaceutically acceptable carriers or diluents under conditions in which aggregation of LIF is reduced.

Still yet another aspect of the present invention provides a composition with improved chemical and physical stability comprising LIF or a derivative or homologue thereof, a stabilizing agent, additives for maintaining pH and isotonicity and one or more pharmaceutically acceptable carriers or diluents under conditions in which deamidation of LIF is reduced.

Analogues and mimetics include molecules which contain non-naturally occurring amino acids or which do not contain amino acids but nevertheless behave functionally the same as or similar to LIF. Natural product screening is one useful strategy for identifying analogues and mimetics. Analogues of LIF contemplated herein also include modifications to side chains, incorporation of unnatural amino acids and/or their derivatives during peptide synthesis and the use of cross linkers and other methods which impose conformational constraints on the protein molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-axnino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |

TABLE 1-continued

| Non-conventional amino acid | Code | Non-conventional amino acid | Code |
|---|---|---|---|
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenylethylamino)cyclopropane | Nmbc | | |

Crosslinkers can be used, for example, to stabilise 3D conformations, using homo-bifunctional crosslinkers such as the bifunctional imido esters having $(CH_2)_n$ groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety(SH) or carbodiimide(COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

All these types of modifications may be important to further stabilise LIF in the composition of the present invention.

The compositions of the present invention achieve their stability through judicious choice of pH conditions within the range of from about 3.5 to about 6.5 inclusive and optionally the presence of one or more suitable stabilizing agents and/or additives. Preferably, the pH range is between from about 4.0–6.0 inclusive, more preferably between from about 4.5 to about 5.5 inclusive. Most preferably, the pH of the composition is about 5.0.

Accordingly, another aspect of the present invention provides a composition comprising Leukaemia Inhibitory Factor (LIF) and one or more pharmaceutically acceptable carriers and/or diluents and wherein the composition has a pH of between about 3.5 and 6.5.

Suitable stabilizing agents are known to those skilled in the art and include agents which increase or maintain the conformational stability of LIF and surfactants. It is understood that one agent may possess more than one stabilizing property and more than one agent may be employed to achieve a stabilizing effect.

Suitable agents are those which maintain approximately the same osmotic pressure as that of cellular fluids, and are known to those skilled in the art. These may include, but are not limited to, polyhydric alcohols such as sorbitol, pharmaceutically acceptable salts such as NaCl, buffer species, sugars and pharmaceutically acceptable polymeric compounds. Suitable surfactants may be anionic, cationic, amphoteric or non-ionic. Preferred surfactants include fatty alcohols such as lauryl, cetyl and stearyl alcohols, glyceryl esters such as the mono-, di- and triglycerides, fatty acid esters of fatty alcohols and esters of other alcohols such as propylene glycol, polyethylene glycol, sorbitol, sucrose and cholesterol. Other suitable agents include the polysorbates such as polysorbates 20, 40, 60 and 80 and sorbitan ester, polyoxyethylene derivatives and pharmaceutically acceptable polyoxyethylene-polyoxypropylene copolymers. Suitable agents which maintain or increase the conformational stability of LIF are also known to the person skilled in the art and include sugars and polyhydric alcohols.

Suitable buffers for attaining the desired pH of the composition will be known to those skilled in the art and include phosphate, citrate and acetate buffers. Preferred buffers are citrate and acetate.

Yet another aspect of the present invention contemplates a method of preparing a composition comprising Leukaemia Inhibitory Factor or a derivative or homologue thereof and which exhibits reduced deamidation and/or aggregation of LIF or a derivative or homologue over time said method comprising admixing LIF or its derivative or homologue with a stabilizing agent.

The compositions of the present invention may be suitable for administration in a variety of forms such as, but not limited to, parenteral (e.g. intravenous, intraperitoneal, intramuscular, intradermal), subcutaneous, nasal, rectal, vaginal, topical, buccal and sublingual.

The carrier and other ingredients of the composition must be pharmaceutically "acceptable" in the sense of being compatible with the other ingredients of the composition and not injurious to the subject. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as a solution an aqueous or non-aqueous liquid; or as an oil-in-water liquid emulsion or a water-in-oil liquid emulsion. The active ingredient may also be presented as a bolus, electuary or paste.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for rectal administration may be presented as a suppository with a suitable base comprising, for example, cocoa butter.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, preservatives and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It is also understood that the compositions of the present invention may also comprise one or more active agents or ingredients such a cytokines e.g. interleukins, CD antigens, colony stimulating factors, interferons and tissue necrosis factor.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

A number of formulations of LIF were investigated in order to establish optimum conditions under which chemical and physical degradation is reduced compared to the currently employed formulation of 3.67 mg/ml in 2 mM phosphate buffer, pH 6.4–6.8.

Ion Exchange (IE), Reversed Phase (RP) and Size Exclusion (SEC) chromatography were used to detect changes in chemical and physical degradation.

Freeze/thaw studies revealed high solubility of LIF, i.e. no aggregation, in formulations in the pH range of 4.0–6.0 examined, the highest being in the pH range of 4.5 to 5.5, with optimized stability at pH 5.0.

Studies of the various solutions over varying periods of storage time (0 to 8 weeks) and at a range of storage temperatures (−80 to 25° C.) revealed optimum stability of the solution was achieved in a preferred pH range of 4.5 to 5.5.

The inventors examined a number of pH levels and additives. Samples at pH 4.0, 4.5, 5.0, 5.5 and 6.0 were prepared in Examples 1 and 2, as described hereinafter, and additional additives, Sorbitol, an isotonicity agent, and Polysorbate 80 (also referred to as Tween-80), as a non-ionic surfactant to reduce non-specific adsorption onto surfaces, including glass, were also included. NaCl was also examined as an isotonicity agent.

LIF is present in the compositions of the invention in effective amounts. Effective amounts include from 0.1 mg/ml to 100 mg/ml. Preferred effective amounts are from 10 mg/ml to 10 mg/ml. Particularly preferred amounts range from 400 mg/ml to 1000 mg/ml.

Suitable amounts of surfactant and isotonic agents may range from 0.001 to 30%. Preferably from 0.01 to 10%, even more preferably from 0.01 to 5.0%.

Particularly preferred compositions are those comprising LIF, sorbitol, polysorbate and a citrate or acetate buffer in the preferred ranges described above.

The present invention further provides for the use of a stabilizing agent in the manufacture of a composition exhibiting improved chemical and/or physical stability of Leukaemia Inhibitory Factor (LIF) or a derivative or homologue thereof.

The invention will now be described with reference to the following non-limiting Examples.

EXAMPLE 1

I. Preliminary Formulation Screening

On the basis of preliminary stability data, it was anticipated that deamidation of LIF would represent the principal pathway for degradation of solutions at neutral to slightly alkaline pH. Solution pH was, therefore, considered to be important and was a primary variable evaluated in these stability studies. Screening studies evaluating LIF stability during freeze/thaw cycling, following filtration, upon contact with vials and syringes and following temperature controlled storage were conducted in the pH range of 4 to 6 using acetate and citrate buffers at low concentrations (10 mM for each). Osmolality was controlled by the addition of sorbitol at a concentration of 5% w/v. To minimise the potential for LIF adsorption to vials, filters, and syringes, 0.01% w/v Polysorbate 80 was added to all preliminary formulations evaluated in this series of studies.

II. Analytical Methods

Three analytical methods were used to assess LIF stability upon storage. A reversed phase assay, using a standard wide pore C8 reversed phase column, was utilised for the purpose of total LIF concentration determination. The reversed phase assay was not stability indicating and therefore was not suitable for the determination of degradation products. A cation ion exchange assay was used to assess degradation products resulting from a change in the charge characteristics of the parent compound as deamidation had previously been determined to be the principal pathway for LIF degradation. A size exclusion assay was also used to detect size related changes (either cleavage, crosslinking, or aggregation) upon storage.

A. Reversed Phase (RP) Assay

Reversed phase chromatography was conducted using a wide pore C8 reversed phase column, and a trifluoroacetic acid/acetonitrile mobile phase with gradient elution. Detection was conducted at 210 nm.

B. Ion-Exchange (IEC) Assay

Ion exchange chromatography was conducted using a cation exchange column, pH 7 phosphate buffer and a salt gradient. Detection was conducted at 280 nm.

C. Size Exclusion (SEC) Assay

Size exclusion chromatography was conducted using a dextrose based size exclusion column with a molecular weight range of 10 to 300 Daltons. The mobile phase was a pH 7.2 phosphate buffer and detection was conducted at 210 nm.

III. Method Validation

A. Reversed Phase (RP) Assay

Using the defined RP conditions, LIF eluted as a sharp, symmetrical peak with a retention time of approximately 37 min as shown in FIG. 1. The RP assay was used for quantitation of total LIF only as the method was not selective for LIF in the presence of degradation (deamidation or dimeric) products.

Calibration curves for total peak area versus LIF concentration were prepared with each set of analyses in the concentration range of 0.2 and 1.0 mg/ml LIF.

Precision was determined from the coefficient of variation (CV, %) for the total peak area obtained for replicate injections of standard solutions prepared at 0.4 and 1.0 mg/ml. Accuracy was determined by comparison of the total peak area for these standard solutions to a separately prepared calibration curve and was expressed as the percentage deviation from the nominal concentration. Results for accuracy and precision with the RP assay are shown in Table 1. A summary of the RP calibration curves is shown in Table 2.

B. Ion-Exchange (IEC) Assay

Figure 2:
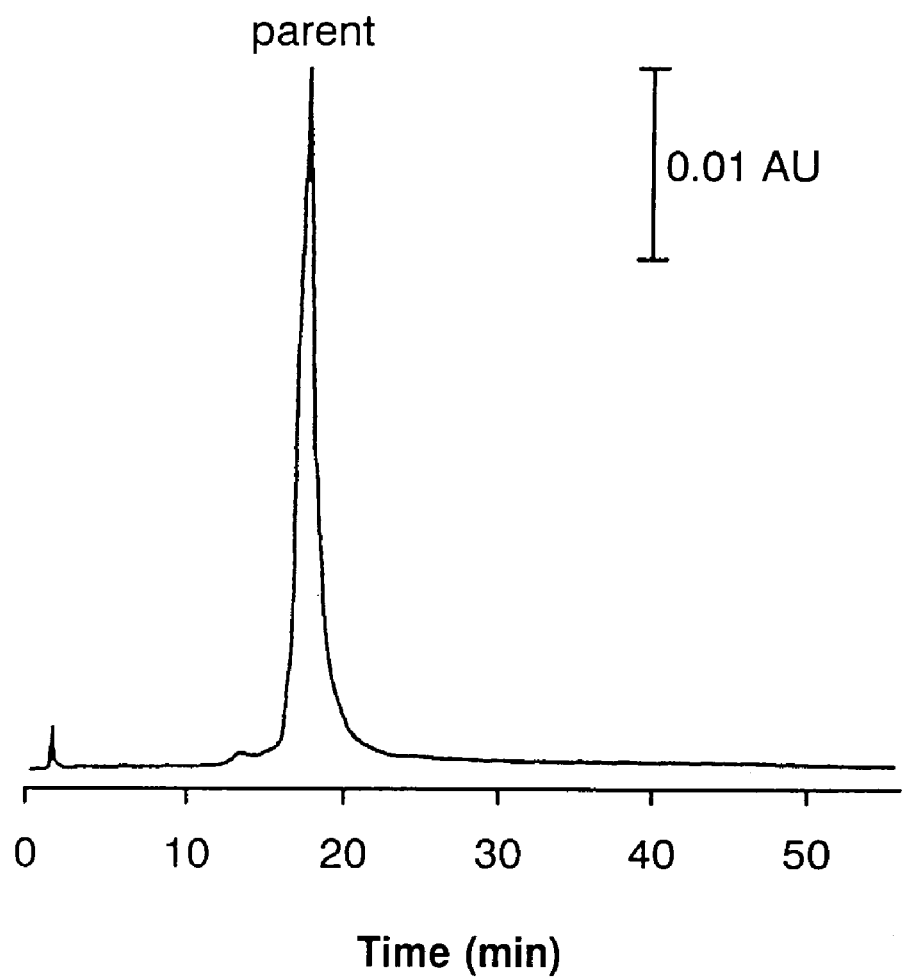

Using the defined IEC conditions, LIF eluted as a slightly tailing peak with a retention time of approximately 13 min as shown in FIG. 2. Separation of the main LIF peak from degradation (deamidation) products formed following storage was observed during the course of the studies. The actual identity of the degradation products (i.e. site of deamidation) was not determined in these studies.

Calibration curves for total peak area (main peak plus degradation products) versus LIF concentration were prepared with each set of analyses in the concentration range of 0.2 and 1.0 mg/ml LIF. Calibration curves were linear in this range when 100 μl was injected onto the column.

Precision was determined from the coefficient of variation (CV, %) for the total peak area obtained for replicate injections of standard solutions prepared at 0.4 and 1.0 mg/ml. Accuracy was determined by comparison of the total peak area for these standard solutions to a separately prepared calibration curve and was expressed as the percentage deviation from the nominal concentration. Results for precision and accuracy for the IEC assay are shown in Table 3. A summary of the IEC calibration curves over the course of the study is shown in Table 4.

C. Size Exclusion (SEC) Assay

Figure 3:
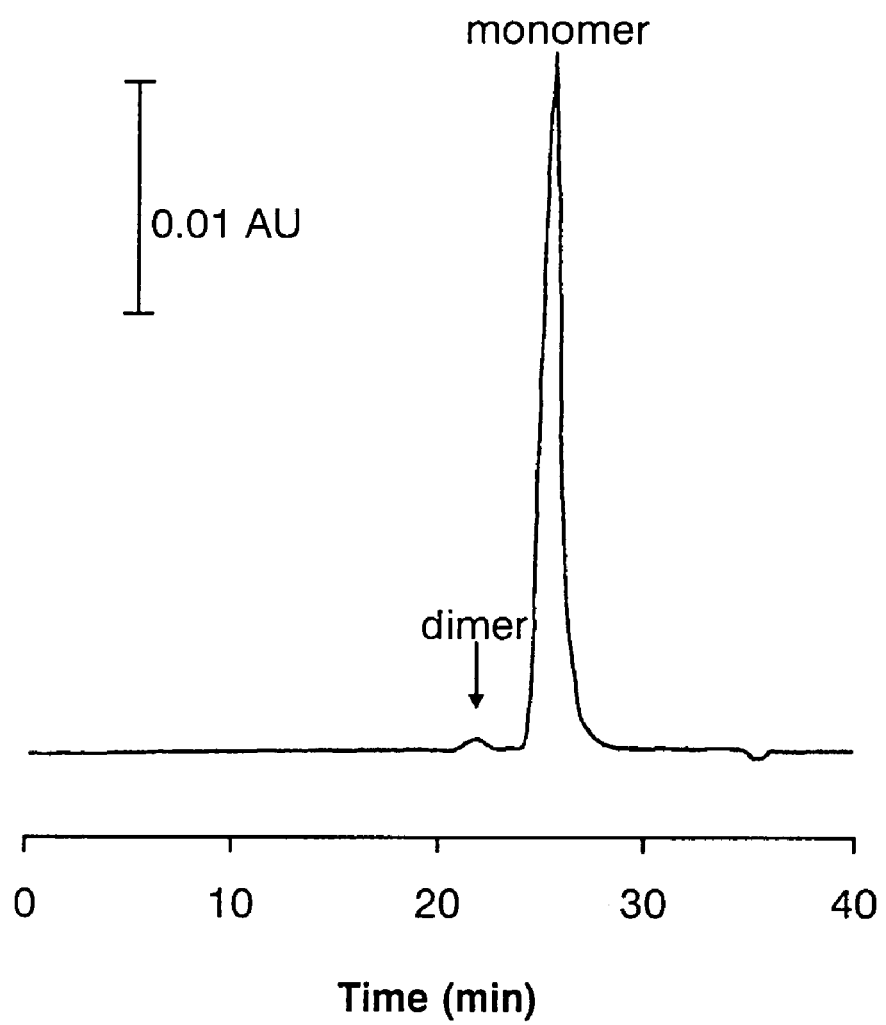
Figure 4A:
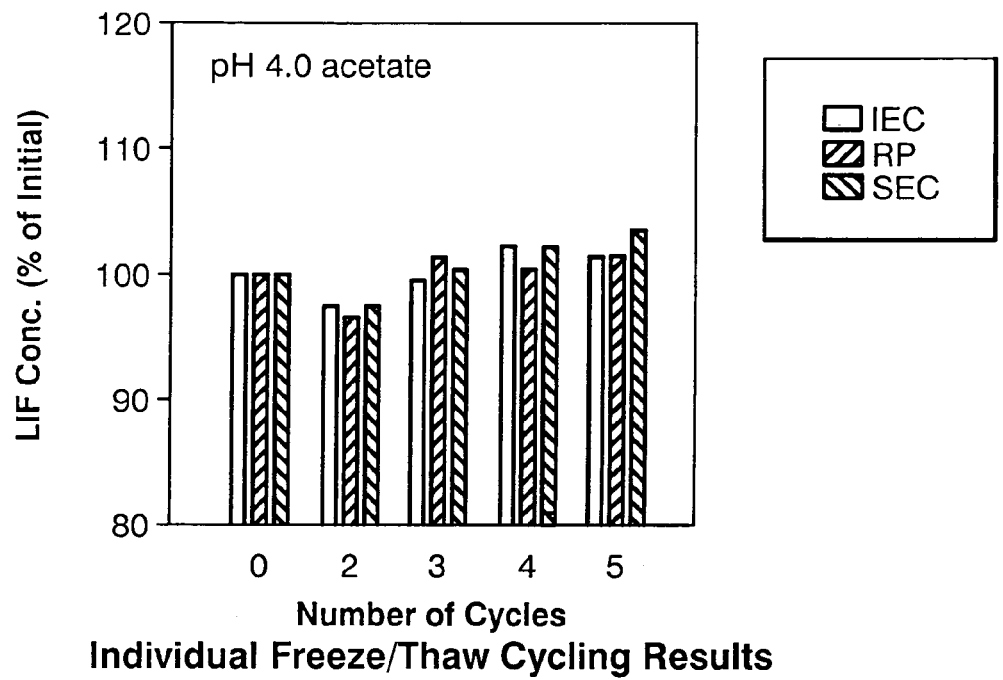
FIGS. 4a–4e are graphical representations showing LIF concentration for samples at each pH after freeze/thaw cycling.
Figure 4B:
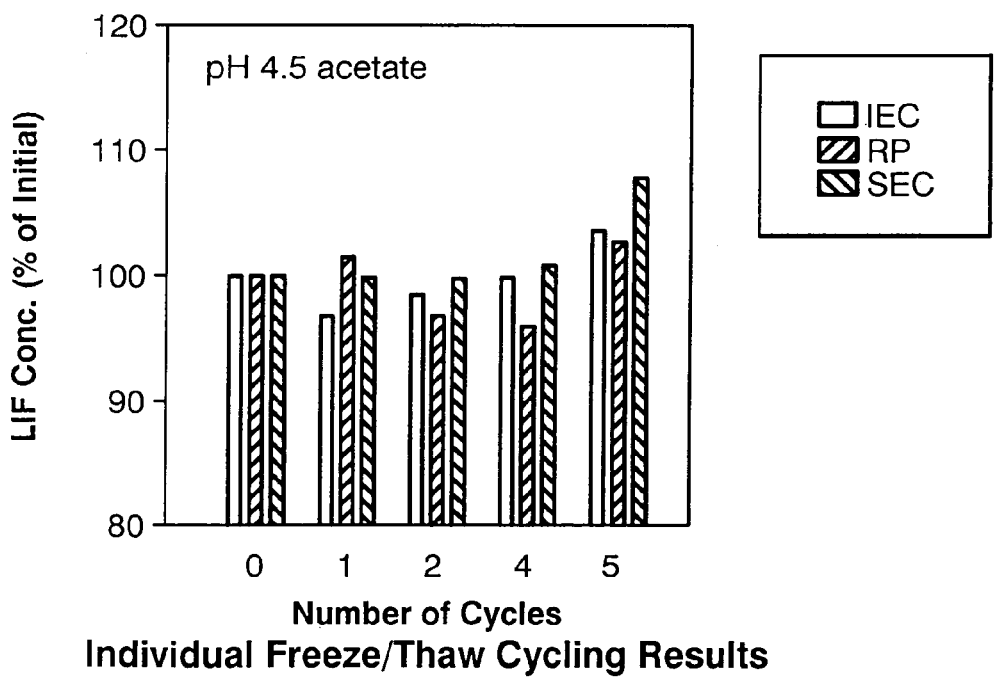
Figure 4C:
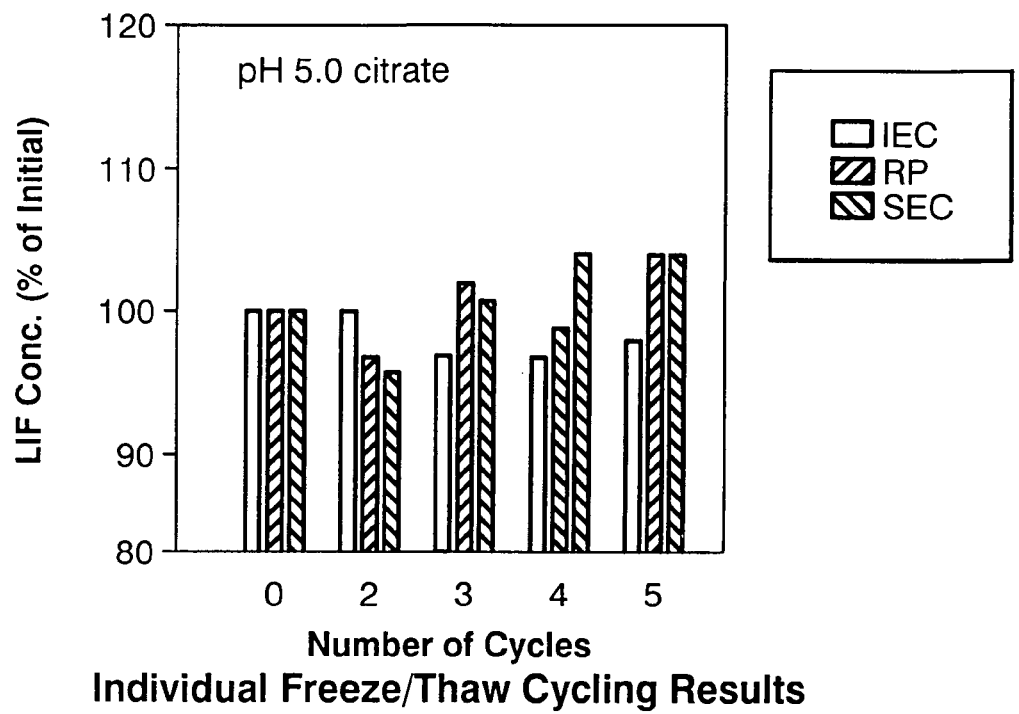
Figure 4D:
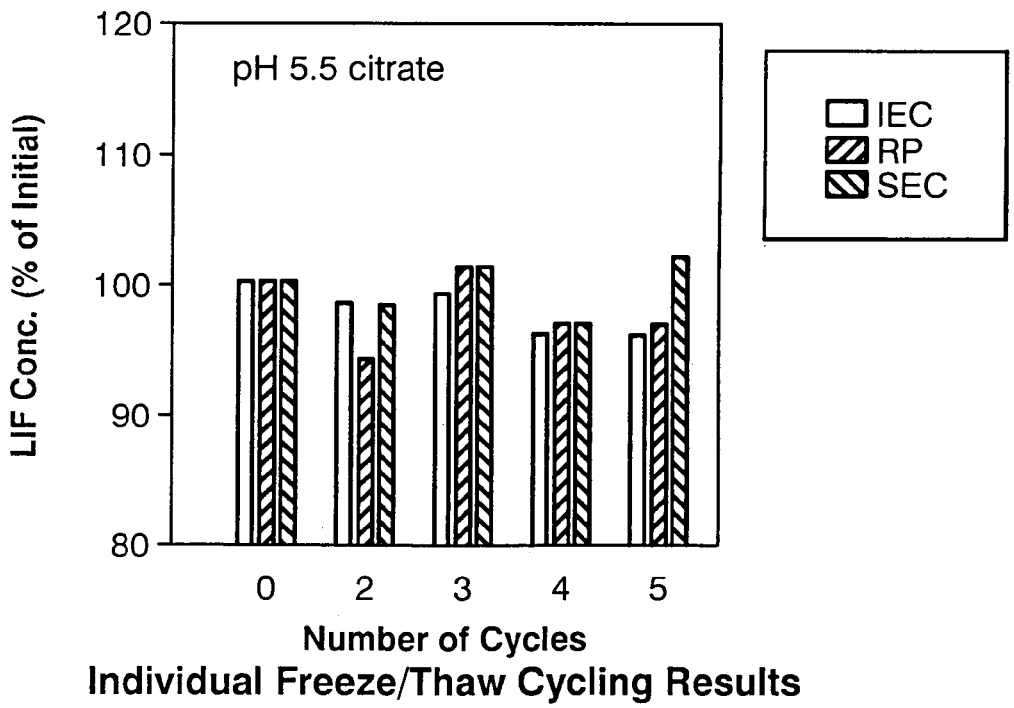
Figure 4E:
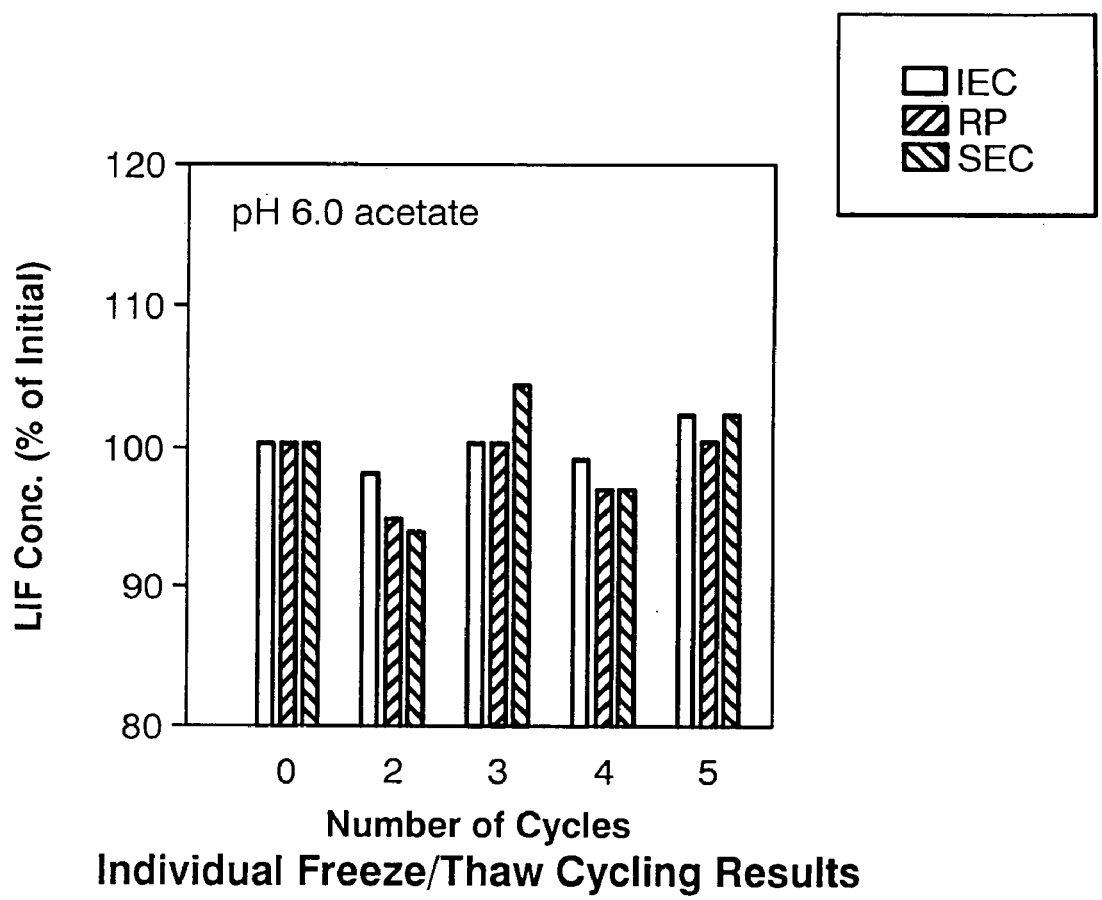

Using the defined SEC conditions, LIF eluted as a sharp, symmetrical peak with a retention time of approximately 26 min as shown in FIG. 3. The method separated monomeric LIF from dimeric LIF which eluted at approximately 21 min, but was not selective for other degradation (deamidation) products which eluted as monomeric LIF.

Calibration curves for total peak area (main peak plus degradation products) versus LIF concentration were prepared with each set of analyses in the concentration range of 0.2 and 1.0 mg/mil LIF.

Precision was determined from the coefficient of variation (CV, %) for the total peak area obtained for replicate injections of standard solutions prepared at 0.4 and 1.0 mg/ml. Accuracy was determined by comparison of the total peak area for these standard solutions to a separately prepared calibration curve and was expressed as the percentage deviation from the nominal concentration. Results for precision and accuracy for the SEC assay are shown in Table 5. A summary of the SEC calibration curves is shown in Table 6.

IV. Buffer Composition

All LIF samples were prepared by dilution of stock LIF solution containing 3.67 mg/ml LIF in 2 mM phosphate buffer, pH 6.42 to give the desired final LIF concentration (either 0.4 or 1.0 mg/ml) and composition of buffer components. In these studies, the final composition of each solution contained 10 mM buffer (either acetate or citrate), 5% w/v sorbitol and 0.01% w/v Polysorbate 80. Samples differed in the final concentration of phosphate buffer (present from the original stock LIF solution) depending on the dilution factor. The 0.4 mg/ml LIF solutions contained 0.22 mM residual phosphate while the 1.0 mg/ml LIF solutions contained 0.54 μM residual phosphate. The composition of each buffer was as follows:

A. Acetate Buffer for 0.4 mg/ml LIF Formulations

Solution A:
  11.22 mM sodium acetate trihydrate (Merck #1.06267)
  5.61% w/v sorbitol (Sigma Chemicals #S1876)
  0.0112% w/v Polysorbate 80 (Sigma Chemicals #P1754)

Solution B:
  11.22 mM glacial acetic acid (Sigma Chemicals #A6283)
  5.61% w/v sorbitol (Sigma Chemicals #S1876)
  0.0112% w/v Polysorbate 80 (Sigma Chemicals #P1754)

Solutions A and B were mixed to give a final pH of 4.0 or 4.5. Formulations were prepared by combining 0.109 parts stock LIF solution and 0.891 parts buffer to give a final LIF concentration of 0.4 mg/ml, a final buffer concentration of 10 mM, a final sorbitol concentration of 5% w/v and a final Polysorbate 80 concentration of 0.01% w/v.

B. Acetate Buffer for 1.0 mg/ml LIF Formulations

Solution A:
  13.75 mM sodium acetate trihydrate (Merck #1.06267)
  6.88% w/v sorbitol (Sigma Chemicals #S1876)
  0.0138% w/v Polysorbate 80 (Sigma Chemicals #P1754)

Solution B:
  13.75 mM glacial acetic acid (Sigma Chemicals #A6283)
  6.88% w/v sorbitol (Sigma Chemicals #S1876)
  0.0138% w/v Polysorbate 80 (Sigma Chemicals #P1754)

Solutions A and B were mixed to give a final pH of 4.0 or 4.5. Formulations were prepared by combining 0.272 parts stock LIF solution and 0.728 parts buffer to give a final LIF concentration of 1.0 mg/ml, a final buffer concentration of 10 mM, a final sorbitol concentration of 5% w/v and a final Polysorbate 80 concentration of 0.01% w/v.

C. Citrate Buffer for 0.4 mg/ml LIF Formulations

Solution A:
- 11.22 mM sodium citrate dihydrate (Merck #1.06448)
- 5.61% w/v sorbitol (Sigma Chemicals #S1876)
- 0.0112% Polysorbate 80 (Sigma Chemicals #P1754)

Solution B:
- 11.22 mM citric acid monohydrate (Merck #1.00244)
- 5.61% w/v sorbitol (Sigma Chemicals #S1876)
- 0.0112% Polysorbate 80 (Sigma Chemicals #P1754)

Solutions A and B were mixed to give a final pH of 5.0, 5.5, or 6.0. Formulations were prepared by combining 0.109 parts stock LIF solution and 0.891 parts buffer to give a final LIF concentration of 0.4 mg/ml, a final buffer concentration of 10 mM, a final sorbitol concentration of 5% w/v and a final Polysorbate 80 concentration of 0.01% w/v.

D. Citrate Buffer for 1.0 mg/ml LIF Formulations

Solution A:
- 13.75 mM sodium citrate (Merck #1.06448)
- 6.88% w/v sorbitol (Sigma Chemicals #S1876)
- 0.0138% w/v Polysorbate 80 (Sigma Chemicals #P1754)

Solution B:
- 13.75 mM citric acid (Merck #1.00244)
- 6.88% w/v sorbitol (Sigma Chemicals S1876)
- 0.0138% w/v Polysorbate 80 (Sigma Chemicals P1754)

Solutions A and B were mixed to give a final pH of 5.0, 5.5, or 6.0. Formulations were prepared by combining 0.272 parts stock LIF solution and 0.728 parts buffer to give a final LIF concentration of 1.0 mg/ml, a final buffer concentration of 10 mM, a final sorbitol concentration of 5% w/v and a final Polysorbate 80 concentration of 0.01% w/v.

Table 7 displays pH and osmolality (obtained using a Fiske One-Ten Osmometer) values for 0.4 and 1.0 mg/mil LIF samples prepared using the above buffer systems.

V. Freeze/Thaw Cycling

A. Sample Preparation and Methods

LIF samples were prepared by dilution of stock LIF (3.67 mg/ml in 2 mM phosphate buffer, pH 6.8) with acetate or citrate buffer containing sorbitol and polysorbate 80 to give a final buffer concentration of 10 mM, a theoretical pH of 4.0, 4.5, 5.0, 5.5, or 6.0, a final sorbitol concentration of 5% w/v, a final polysorbate 80 concentration of 0.01% w/v and a final LIF concentration of 1 mg/ml (see Section IV). The final pH of each sample was essentially the same as predicted by theory. Solutions (3 ml) were filtered through 0.22 μm sterile filters (Millex GV) with the first 0.5 ml aliquot from the filter being retained as a separate sample for the preliminary determination of filter adsorption. Subsequent 0.5 ml aliquots were filtered into sterile 2 ml glass vials and capped with sterile rubber/teflon lined caps and crimped. One vial for each formulation was analysed on the day of preparation and all other vials were stored at −80° C. On each of 5 days, all vials were thawed and one vial of each formulation was centrifuged and an aliquot taken for dilution (in this study, all samples were analysed at a LIF concentration of 0.1 mg/ml) and analysis by RP, IEC, and SEC.

A 0.1 mg/ml standard solution was prepared by diluting the LIF stock solution with 2 mM phosphate buffer, pH 6.42 containing 0.01% polysorbate 80. This standard solution was stored at 4° C. for a total of 6 days and analysed along with each sample set.

B. Results

FIGS. 4a–4e represent the individual results for samples at each pH with concentration being expressed as a percentage of the initial concentration measured by each of the three methods.

While there was some variability in the individual results (most likely due to the dilution step prior to analysis), there were no trends which would indicate loss of LIF upon freeze/thaw cycling.

Figure 5:
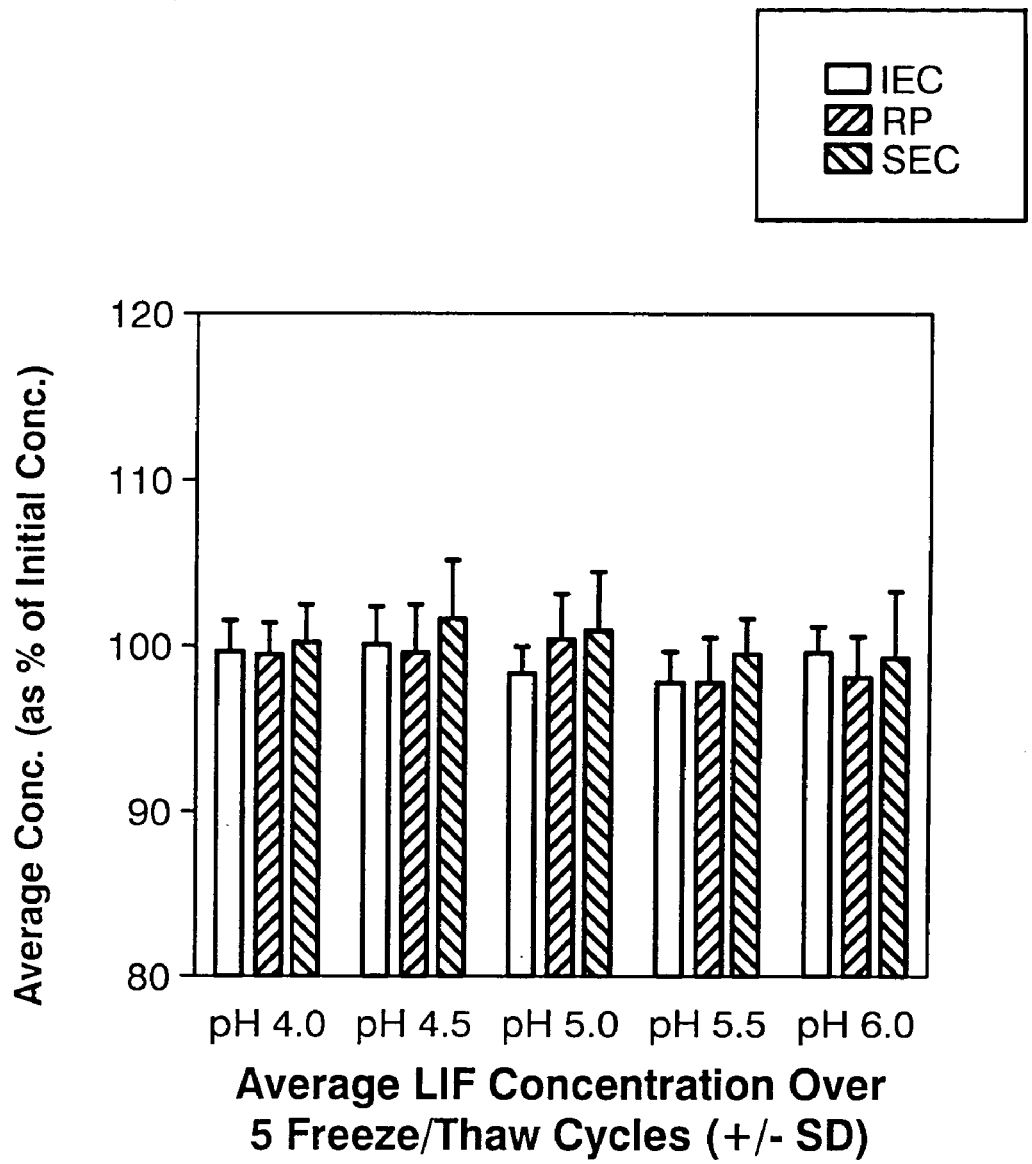
FIG. 5 is a graphical representation of the average concentration over 5 freeze/thaw cycles for each pH value.

FIG. 5 illustrates the average concentration (as a percentage of the initial concentration) over 5 freeze/thaw cycles for each of the different pH values.

VI. Long Term Stability at −80° C., −20° C., 8° C. and 25° C.

A. Preparation of Samples for Storage at −80° C. and −20° C.

Five LIF formulations were prepared by dilution of stock LIF (3.67 mg/ml in 2 mM phosphate buffer, pH 6.42) with acetate or citrate buffer containing sorbitol and polysorbate 80 to give a final LIF concentration of 0.4 mg/ml or 1.0 mg/ml, a final buffer concentration of 10 mM, a final sorbitol concentration of 5% w/v and a final polysorbate 80 concentration of 0.01% w/v (see Section V). The theoretical pH values were pH 4.0 (acetate buffer), 4.5 (acetate buffer), and 5.0 (citrate buffer). The final pH of each sample was essentially the same as predicted by theory.

Under aseptic conditions in a laminar flow cabinet, the formulations were sterile filtered using 0.22 μm Millex GV (Millipore) filters. The first 1.0 ml of each filtrate was set aside and the vial marked accordingly (previous studies identified that approximately 1 ml was required to saturate the filter binding sites using Millex GV filter units). The remaining volume was filtered into a sterile 50 ml polypropylene tube. Aliquots of each formulation (1.15 ml/vial) were transferred using a multiple dispensing Eppendorf pipette with sterile tips into heat sterilised 2 ml glass vials and capped with sterile teflon lined rubber caps which were then crimped. Vials were labelled and duplicate vials of each formulation were retained for the initial analysis. The remaining vials were stored at either −80° C. or −20° C.

B. Preparation of Samples for Storage at 8° C. and 25° C.

Five LIF formulations were prepared by a dilution of stock LIF (3.67 mg/ml in 2 mM phosphate buffer, pH 6.42) with acetate or citrate buffer containing sorbitol and polysorbate 80 to give a final LIF concentration of 0.4 mg/ml or 1.0 mg/ml, a final buffer concentration of 10 mM, a final sorbitol concentration of 5% w/v and a final polysorbate 80 concentration of 0.01% w/v. The theoretical pH values were pH 4.0 (acetate buffer), 4.5 (acetate buffer), and 5.0 (citrate buffer). The final pH of each sample was essentially the same as predicted by theory.

Formulations were filtered and filled into vials as described for the −80° C. and −20° C. samples. Samples were stored in temperature controlled incubators at either 8° C. or 25° C. Incubators were checked daily to ensure the correct temperature was maintained.

C. Sample Analysis

All LIF samples were analysed undiluted according to the methods described in Section m. LIF standards at concentrations of 0.2, 0.4, 0.7 and 1.0 mg/ml were prepared from stock LIF (3.67 mg/ml in 2 mM phosphate buffer) by diluting with 2 mM phosphate buffer, pH 6.42 containing 0.01% w/v polysorbate 80. These standards were prepared fresh at the beginning of each set of analyses and were analysed along with the samples at the start and end of each analytical run.

At each time point, 2 vials were withdrawn from the freezers or incubators and approximately 200 µl was removed from each using a sterile 1 ml syringe and a sterile needle. These aliquots were placed into polypropylene autosampler vials and sealed with caps containing self-sealing septa to allow repeat injections from the same vial without evaporation.

Autosampler vials were transferred to the autosampler where they were maintained at 4° C. throughout the three analytical runs. The same sample and standard autosampler vials were used for each of the three analyses with the RP (10 µl injection volume) being conducted first, followed by the IEC (100 µl injection volume) and then the SEC (10 µl injection volume). The complete RP run took approximately 32 hours, and the IEC and SEC runs took approximately 25 hours each. It was assumed that any further degradation over this storage time in the autosampler would be minimal (standard solutions at pH 6.42 stored under the same conditions showed no change over the complete analytical period). Samples were analysed in the following order:

| | |
|---|---|
| Blank × 2 | |
| Standards | 0.2 mg/ml, 0.4 mg/ml, 0.7 mg/ml and 1.0 mg/ml |
| Blank | |
| 0.4 mg/ml | Acetate pH 4.0 × 2 |
| | Acetate pH 4.5 × 2 |
| | Citrate pH 5.0 × 2 |
| 1.0 mg/ml | Acetate pH 4.5 × 2 |
| | Citrate pH 5.0 × 2 |
| Blank | |
| Standards | 0.2 mg/ml, 0.4 mg/ml, 0.7 mg/ml and 1.0 mg/ml |

Selected samples were also analysed for particulates using a Malvern Instruments Zetasizer 3000 particle size instrument. Samples were withdrawn from the storage vials using a syringe and placed in the sample cuvette. Samples were counted for 120 sec using a 200 µm pinhole (to obtain the maximum signal), 90° scattering angle, and scattering source at 633 nm using a 10 mW He—Ne ion laser.

D. Results

Data pertaining to solution pH, LIF concentration in mg/ml (determined by comparison to LIF standard solutions), and the area % of the main peak relative to the total peak area for all LIF related peaks in the chromatogram analysed using the three chromatographic methods are shown in Tables 8 through 17. None of the samples showed significant shifts in pH over the storage period.

1. Ion Exchange

IEC chromatograms for samples stored in each of the different buffer systems at 8 and 25° C. showed two main products for samples prepared in pH 4.0 and 4.5 buffers (eluting at approximately 9 and 10 min) whereas a single main product (eluting at approximately 10 min) was seen in the pH 5.0 samples. At each pH, there was evidence of several minor degradation products in the ion exchange chromatograms, however, due to inadequate resolution between the different products, the exact number of products could not be determined. Representative chromatograms for samples stored at −80 and −20° C. are not shown as they were similar to the chromatograms at the higher temperatures with degradation products being present at significantly reduced levels.

The IEC results for samples stored at −80, −20, 8 and 25° C. illustrate the dependence of LIF stability on pH and temperature (Tables 8–17). The relative stability under each storage condition was similar for the 0.4 and 1.0 mg/ml formulations. The pH 4.0 samples displayed significant variability between the different time points at 8 and 25° C. Re-analysis of selected samples gave similar results to the original values. There was also evidence of degradation at pH 4.0 and 4.5 following storage at −20° C. and −80° C. The stability was greatly improved at pH 5 in comparison to pH 4 and 4.5. At pH 5.0 after 55 days storage at 8° C., approximately 97% of the total peak area was present as the main LIF peak. Following storage at 25° C. for 55 days, this value was reduced to approximately 78%. Samples prepared at pH 5 and stored at −80 or −20° C. for up to 84 days showed no significant evidence of degradation.

2. Reversed Phase

Representative RP chromatograms are not included as all displayed essentially the same elution characteristics (see FIG. 1). In all cases, the chromatograms showed the presence of only one main peak eluting at approximately 36 min.

The RP results for samples stored at −80, −20, 8 and 25° C., wherein the measured concentration was plotted as a function of storage time, illustrated the absence of significant change in the measured concentration over the storage period for each of the buffer and storage conditions utilised.

3. Size Exclusion

SEC chromatograms for the samples as all displayed essentially the same elution characteristics (see FIG. 3). In all cases, the chromatograms showed the presence of one main peak eluting at approximately 26 min and a minor peak eluting at approximately 21 min.

The SEC results for samples stored at −80, −20, 8 and 25° C. wherein the measured concentration was plotted as a function of storage time, illustrated the absence of significant change in the measured concentration over the storage period for each of the buffer and storage conditions utilised. Using the SEC method, there was no evidence of chain cleavage or crosslinking under the storage conditions studied.

4. Particle Size Analysis

Samples stored for 56 days at −80 and −20° C. and for 41 days at 8 and 25° C. were analysed for particulates using a laser light scattering instrument. All of the samples analysed displayed a count rate of "0 kCps" which effectively means that the samples contained no particulates (i.e. no signal was measurable).

VII. Summary

These studies demonstrated no notable loss of LIF following freeze thaw cycling of 1.0 mg/ml LIF solution formulations prepared in acetate or citrate buffers (pH 4 to 6) containing 5% w/v sorbitol and 0.01% w/v polysorbate 80. There was no significant loss of LIF on 0.2 µm Sartorius Minisart filters when formulations were prepared at either 0.4 or 1.0 mg/ml in pH 5.0 or 5.5 citrate buffers containing 5% w/v sorbitol and 0.01% w/v polysorbate 80. For the pH 5.0 and 5.5 formulations, there was also no evidence of loss of LIF on the proposed vials, stoppers, or syringes.

At −80° C., there was no significant change in LIF concentrations measured by RP, IEC and SEC methods following storage for 84 days in the pH range of 4 to 5. At −20° C. over the same time period, there was evidence of degradation for formulations prepared at pH 4 and analysed by EC, but the remaining formulations were stable under these storage conditions. Generally, 0.4 and 1.0 mg/ml LIF formulations displayed similar stability characteristics under each of the conditions investigated. Formulations prepared at pH 5 were found to be stable for up to 8 weeks when stored at 8° C. with minimal loss of the parent compound (~1%) shown by IEC and no loss shown by RP or SEC.

TABLE 1

Precision and Accuracy for the RP Assay

| Nominal Conc. (mg/ml) | Total Peak Area | Measured Conc. (mg/ml) | Precision (CV, %) | Accuracy (% deviation) |
|---|---|---|---|---|
| 0.4 | 14.213 | 0.391 | 0.44 (n = 5) | −2.16 |
| 0.4 | 14.356 | 0.395 | | −1.21 |
| 0.4 | 14.361 | 0.395 | | −1.17 |
| 0.4 | 14.322 | 0.394 | | −1.43 |
| 0.4 | 14.255 | 0.392 | | −1.88 |
| 1.0 | 38.002 | 1.029 | 0.39 (n = 5) | 2.92 |
| 1.0 | 38.170 | 1.034 | | 3.37 |
| 1.0 | 38.327 | 1.038 | | 3.79 |
| 1.0 | 38.344 | 1.038 | | 3.84 |
| 1.0 | 38.077 | 1.031 | | 3.12 |

TABLE 2

Summary of RP Calibration Curves Over the Course of the Study

| | Slope | Intercept |
|---|---|---|
| | 33.460 | −1.755 |
| | 32.900 | −0.312 |
| | 34.491 | −1.040 |
| | 32.648 | −0.137 |
| | 32.865 | 1.006 |
| | 32.865 | 0.566 |
| | 33.705 | 1.092 |
| | 34.617 | 0.535 |
| | 35.920 | 0.113 |
| | 35.666 | −0.014 |
| | 37.294 | −0.382 |
| mean | 34.221 | −0.030 |
| SD | 1.529 | |
| CV, % | 4.469 | |

TABLE 3

Precision and Accuracy for the IEC Assay

| Nominal Conc. (mg/ml) | Total Peak Area | Measured Conc. (mg/ml) | Precision (CV, %) | Accuracy (% deviation) |
|---|---|---|---|---|
| 0.4 | 8.310 | 0.397 | 0.68 (n = 5) | −0.86 |
| 0.4 | 8.260 | 0.398 | | −0.62 |
| 0.4 | 8.265 | 0.399 | | −0.30 |
| 0.4 | 8.232 | 0.396 | | −1.10 |
| 0.4 | 8.234 | 0.403 | | 0.65 |
| 1.0 | 21.929 | 1.007 | 0.41 (n = 5) | 0.70 |
| 1.0 | 21.910 | 1.005 | | 0.51 |
| 1.0 | 21.918 | 1.008 | | 0.77 |
| 1.0 | 21.901 | 1.004 | | 0.35 |
| 1.0 | 21.870 | 1.014 | | 1.43 |

TABLE 4

Summary of IEC Calibration Curves Over the Course of the Study

| | Slopes | Intercept |
|---|---|---|
| | 2.953 | −0.002 |
| | 3.111 | −0.038 |
| | 3.104 | −0.048 |
| | 2.983 | −0.019 |
| | 2.987 | −0.020 |
| | 3.005 | −0.018 |
| | 2.942 | −0.012 |
| | 3.064 | −0.055 |
| | 3.005 | −0.018 |
| | 3.034 | −0.036 |
| | 3.137 | −0.099 |
| mean | 3.030 | −0.033 |
| SD | 0.066 | — |
| CV, % | 2.180 | — |

TABLE 5

Precision and Accuracy for the SEC Assay

| Nominal Conc. (mg/ml) | Total Peak Area | Measured Conc. (mg/ml) | Precision (CV, %) | Accuracy (% deviation) |
|---|---|---|---|---|
| 0.4 | 8.310 | 0.396 | 0.39 (n = 5) | −0.98 |
| 0.4 | 8.260 | 0.394 | | −1.48 |
| 0.4 | 8.265 | 0.394 | | −1.46 |
| 0.4 | 8.232 | 0.393 | | −1.84 |
| 0.4 | 8.234 | 0.393 | | −1.86 |
| 1.0 | 21.929 | 1.002 | 0.11 (n = 5) | 0.23 |
| 1.0 | 21.910 | 1.001 | | 0.11 |
| 1.0 | 21.918 | 1.001 | | 0.15 |
| 1.0 | 21.901 | 1.000 | | 0.07 |
| 1.0 | 21.870 | 0.999 | | −0.05 |

TABLE 6

Summary of SEC Calibration Curves Over the Course of the Study

| | Slope | Intercept |
|---|---|---|
| | 21.332 | 0.202 |
| | 21.278 | 0.166 |
| | 22.351 | 0.230 |
| | 21.672 | 0.054 |
| | 20.810 | 0.419 |
| | 21.561 | 0.130 |
| | 21.845 | 0.074 |
| | 21.883 | −0.090 |
| | 21.963 | 0.158 |
| | 21.794 | −0.003 |
| | 22.558 | −0.474 |
| mean | 21.732 | 0.079 |
| SD | 0.491 | — |
| CV, % | 2.258 | — |

TABLE 7 pH and Osmolality of AM424 Formulations

| buffer/theoretical pH | AM424 conc. (mg/ml) | measured pH | osmolality (mOsm/kg) |
|---|---|---|---|
| Acetate/pH 4.0 | 0.4 | 3.95 | 297 |
| Acetate/pH 4.5 | 0.4 | 4.48 | 297 |
| Citrate/pH 5.0 | 0.4 | 4.94 | 303 |
| Acetate/pH 4.5 | 1.0 | 4.47 | 294 |
| Citrate/pH 5.0 | 1.0 | 4.96 | 305 |

TABLE 8

Summary of 0.4 mg/ml, pH 4.0 AM424 Formulation Stability Following Storage at 8° C. and 25° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.03 | acetate | 0.4 | 8 | 0 | 0.40, 0.39 | 100, 100 | 0.37, 0.37 | 98.9, 99.0 | 0.39, 0.40 | 98.8, 98.7 |
| — | | | | 7 | 0.40, 0.40 | 100, 100 | 0.35, 0.34 | 91.7, 87.2 | 0.39, 0.40 | 97.6, 97.5 |
| 4.07 | | | | 13 | 0.39, 0.39 | 100, 100 | 0.33, 0.37 | 90.8, 92.8 | 0.40, 0.40 | 98.9, 98.9 |
| — | | | | 19 | 0.40, 0.40 | 100, 100 | 0.34, 0.33 | 89.7, 86.8 | 0.38, 0.38 | 98.8, 99.0 |
| 4.06 | | | | 27 | 0.40, 0.40 | 100, 100 | 0.33, 0.33 | 84.6, 83.7 | 0.40, 0.40 | 98.9, 98.9 |
| 4.06 | | | | 41 | 0.40, 0.40 | 100, 100 | 0.34, 0.35 | 86.9, 88.2 | 0.40, 0.41 | 98.9, 98.9 |
| 4.16 | | | | 55 | 0.40, 0.41 | 100, 100 | 0.34, 0.33 | 89.2, 83.0 | 0.40, 0.40 | 99.0, 99.0 |
| 4.03 | acetate | 0.4 | 25 | 0 | 0.40, 0.39 | 100, 100 | 0.37, 0.37 | 98.9, 99.0 | 0.39, 0.40 | 98.8, 98.7 |
| — | | | | 7 | 0.39, 0.39 | 100, 100 | 0.33, 0.36 | 85.1, 91.5 | 0.39, 0.40 | 97.3, 97.4 |
| 4.06 | | | | 13 | 0.40, 0.39 | 100, 100 | 0.28, 0.30 | 74.7, 80.7 | 0.39, 0.41 | 99.2, 99.1 |
| — | | | | 19 | 0.40, 0.39 | 100, 100 | 0.31, 0.32 | 78.3, 80.3 | 0.38, 0.38 | 99.0, 99.2 |
| 4.07 | | | | 27 | 0.40, 0.40 | 100, 100 | 0.29, 0.30 | 73.3, 74.5 | 0.40, 0.40 | 99.4, 99.2 |
| 4.09 | | | | 41 | 0.40, 0.40 | 100, 100 | 0.31, 0.31 | 76.1, 77.8 | 0.41, 0.41 | 99.2, 99.2 |
| 4.12 | | | | 55 | 0.41, 0.40 | 100, 100 | 0.25, 0.24 | 62.6, 59.8 | 0.40, 0.40 | 99.3, 99.7 |

Underlined values represent repeat analyses

TABLE 9

Summary of 0.4 mg/ml, pH 4.0 AM424 Formulation Stability Following Storage at −80° C. and −20° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 3.95 | acetate | 0.4 | −80 | 0 | 0.41, 0.40 | 100, 100 | 0.38, 0.38 | 98.4, 98.6 | 0.40, 0.40 | 98.9, 98.5 |
| 3.98 | | | | 28 | 0.41, 0.41 | 100, 100 | 0.38, 0.39 | 97.8, 98.8 | 0.39, 0.40 | 98.2, 98.0 |
| 3.99 | | | | 56 | 0.41, 0.41 | 100, 100 | 0.37, 0.38 | 96.6, 98.9 | 0.39, 0.39 | 98.3, 98.3 |
| 4.05 | | | | 84 | 0.43, 0.42 | 100, 100 | 0.40, 0.38 | 98.6, 99.1 | 0.41, 0.41 | 99.3, 98.6 |
| 3.95 | acetate | 0.4 | −20 | 0 | 0.41, 0.40 | 100, 100 | 0.38, 0.38 | 98.4, 98.6 | 0.40, 0.40 | 98.9, 98.5 |
| 3.95 | | | | 28 | 0.41, 0.42 | 100, 100 | 0.38, 0.39 | 96.9, 97.8 | 0.40, 0.40 | 98.7, 98.5 |
| 4.04 | | | | 56 | 0.40, 0.41 | 100, 100 | 0.36, 0.36 | 94.2, 93.7 | 0.40, 0.40 | 99.0, 98.9 |
| 4.03 | | | | 84 | 0.42, 0.43 | 100, 100 | 0.38, 0.38 | 92.5, 93.1 | 0.42, 0.41 | 99.2, 98.9 |

TABLE 10

Summary of 0.4 mg/ml, pH 4.5 AM424 Formulation Stability Following Storage at 8° C. and 25° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.52 | acetate | 0.4 | 8 | 0 | 0.39, 0.39 | 100, 100 | 0.36, 0.36 | 99.0, 98.9 | 0.39, 0.38 | 98.8, 98.8 |
| — | | | | 7 | 0.38, 0.38 | 100, 100 | 0.37, 0.36 | 95.4, 95.6 | 0.38, 0.39 | 97.7, 97.8 |
| 4.53 | | | | 13 | 0.38, 0.38 | 100, 100 | 0.38, 0.36 | 98.3, 95.6 | 0.39, 0.38 | 99.0, 99.0 |
| — | | | | 19 | 0.38, 0.38 | 100, 100 | 0.37, 0.35 | 97.8, 93.3 | 0.38, 0.38 | 98.2, 98.2 |
| 4.53 | | | | 27 | 0.38, 0.38 | 100, 100 | 0.35, 0.36 | 90.8, 94.1 | 0.39, 0.39 | 98.9, 98.8 |
| 4.51 | | | | 41 | 0.39, 0.39 | 100, 100 | 0.37, 0.36 | 95.3, 94.2 | 0.39, 0.39 | 98.9, 98.8 |
| 4.59 | | | | 55 | 0.40, — | 100, — | 0.35, 0.33 | 89.6, 85.9 | 0.39, 0.39 | 99.0, 98.9 |
| 4.52 | acetate | 0.4 | 25 | 0 | 0.39, 0.39 | 100, 100 | 0.36, 0.36 | 99.0, 98.9 | 0.39, 0.39 | 98.8, 98.8 |
| — | | | | 7 | 0.38, 0.38 | 100, 100 | 0.36, 0.34 | 94.7, 88.8 | 0.39, 0.39 | 98.1, 98.2 |
| 4.52 | | | | 13 | 0.39, 0.38 | 100, 100 | 0.33, 0.35 | 86.8, 91.0 | 0.39, 0.38 | 99.0, 99.0 |
| — | | | | 19 | 0.38, 0.38 | 100, 100 | 0.31, 0.30 | 82.0, 80.0 | 0.38, 0.38 | 99.1, 99.0 |
| 4.52 | | | | 27 | 0.38, 0.38 | 100, 100 | 0.30, 0.29 | 75.8, 73.5 | 0.39, 0.39 | 99.1, 99.2 |
| 4.53 | | | | 41 | 0.40, 0.40 | 100, 100 | 0.28, 0.28 | 71.2, 71.1 | 0.39, 0.39 | 99.2, 99.3 |
| 4.55 | | | | 55 | 0.39, 0.40 | 100, 100 | 0.22, 0.24 | 53.4, 59.1 | 0.39, 0.39 | 99.3, 99.4 |

Underlined values represent repeat analyses

TABLE 11

Summary of 0.4 mg/ml, pH 1.5 AM424 Formulation Stability Following Storage at −80° C. and −20° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.48 | acetate | 0.4 | −80 | 0 | 0.40, 0.40 | 100, 100 | 0.39, 0.40 | 99.0, 98.9 | 0.40, 0.40 | 98.9, 98.8 |
| 4.49 | | | | 28 | 0.41, 0.40 | 100, 100 | 0.39, 0.38 | 98.7, 98.7 | 0.40, 0.39 | 98.1, 98.0 |
| 4.49 | | | | 56 | 0.40, 0.40 | 100, 100 | 0.38, 0.38 | 98.5, 98.6 | 0.39, 0.39 | 98.4, 98.2 |
| 4.55 | | | | 84 | 0.42, 0.42 | 100, 100 | 0.40, 0.40 | 98.6, 98.4 | 0.42, 0.42 | 98.5, 98.5 |
| 4.48 | acetate | 0.4 | −20 | 0 | 0.40, 0.40 | 100, 100 | 0.39, 0.40 | 99.0, 98.9 | 0.40, 0.40 | 98.9, 98.8 |
| 4.47 | | | | 28 | 0.41, 0.41 | 100, 100 | 0.39, 0.38 | 98.8, 96.9 | 0.40, 0.40 | 98.4, 98.6 |
| 4.52 | | | | 56 | 0.40, 0.40 | 100, 100 | 0.39, 0.38 | 98.5, 97.3 | 0.40, 0.39 | 98.6, 98.7 |
| 4.53 | | | | 84 | 0.42, 0.42 | 100, 100 | 0.40, 0.40 | 96.4, 96.5 | 0.42, 0.42 | 99.0, 99.0 |

TABLE 12

Summary of 1.0 mg/ml, pH 4.5 AM424 Formulation Stability Following Storage at 8° C. and 25° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.54 | acetate | 1.0 | 8 | 0 | 0.99, 0.99 | 100, 100 | <u>0.96, 0.96</u> | 98.5, 98.6 | 0.99, 0.99 | 98.6, 98.2 |
| — | | | | 7 | <u>0.98, 0.98</u> | 100, 100 | <u>0.98, 0.99</u> | 96.9, 979 | <u>0.99, 0.99</u> | 98.6, 98.6 |
| 4.57 | | | | 13 | 0.98, 0.98 | 100, 100 | <u>0.94, 0.96</u> | 96.2, 97.6 | 0.98, 0.98 | 98.8, 98.7 |
| — | | | | 19 | 0.98, 1.00 | 100, 100 | 0.96, 0.94 | 97.5, 95.6 | 1.00, 0.99 | 98.6, 98.8 |
| 4.56 | | | | 27 | 0.99, 1.00 | 100, 100 | <u>0.94, 0.88</u> | 97.0, 90.1 | 1.00, 1.00 | 98.6, 98.8 |
| 4.55 | | | | 41 | 0.98, 0.99 | 100, 100 | 0.88, 0.90 | 90.3, 92.1 | 0.98, 0.98 | 98.9, 98.9 |
| 4.61 | | | | 55 | 0.99, 1.00 | 100, 100 | 0.90, 0.85 | 91.2, 86.1 | 0.99, 0.99 | 98.9, 98.9 |
| 4.54 | acetate | 1.0 | 25 | 0 | 0.99, 0.99 | 100, 100 | <u>0.96, 0.96</u> | 98.5, 98.6 | 0.99, 0.99 | 98.6, 98.2 |
| — | | | | 7 | <u>0.99, 0.99</u> | 100, 100 | <u>0.92, 0.94</u> | 91.4, 92.7 | <u>0.99, 0.99</u> | 98.9, 98.9 |
| 4.57 | | | | 13 | 1.00, 0.99 | 100, 100 | <u>0.82, 0.86</u> | 83.6, 86.6 | 0.98, 0.98 | 99.0, 99.0 |
| — | | | | 19 | 1.00, 1.00 | 100, 100 | 0.84, 0.81 | 83.7, 80.9 | 1.00, 1.00 | 98.9, 98.9 |
| 4.57 | | | | 27 | 1.00, 1.00 | 100, 100 | 0.78, 0.81 | 77.1, 79.3 | 1.00, 1.00 | 99.0, 99.0 |
| 4.59 | | | | 41 | 0.99, 0.99 | 100, 100 | 0.68, 0.65 | 66.4, 63.9 | 0.98, 0.98 | 98.9, 99.1 |
| 4.61 | | | | 55 | 1.00, 0.99 | 100, 100 | 0.59, 0.60 | 56.7, 58.9 | 0.99, 0.99 | 99.1, 99.1 |

Underlined values represent repeat analyses

TABLE 13

Summary of 1.0 mg/ml, pH 4.5 AM424 Formulation Stability Following Storage at −80° C. and −20° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.47 | acetate | 1.0 | −80 | 0 | 1.00, 1.00 | 100, 100 | 0.97, 0.98 | 98.9, 98.7 | 0.99, 0.99 | 98.7, 98.6 |
| 4.47 | | | | 28 | 1.00, 1.00 | 100, 100 | 0.97, 0.97 | 98.4, 98.3 | 0.99, 0.99 | 98.4, 98.4 |
| 4.50 | | | | 56 | 0.99, 0.98 | 100, 100 | 0.96, 0.95 | 98.5, 98.3 | 0.97, 0.97 | 98.5, 98.6 |
| 4.53 | | | | 84 | 1.00, 1.00 | 100, 100 | 0.96, 0.96 | 98.3, 98.5 | 0.98, 0.98 | 98.6, 98.4 |
| 4.47 | acetate | 1.0 | −20 | 0 | 1.00, 1.00 | 100, 100 | 0.97, 0.98 | 98.9, 98.7 | 0.99, 0.99 | 98.7, 98.6 |
| 4.48 | | | | 28 | 1.00, 0.99 | 100, 100 | 0.98, 0.97 | 98.3, 97.4 | 1.00, 0.99 | 98.5, 98.6 |
| 4.50 | | | | 56 | 0.98, 0.99 | 100, 100 | 0.94, 0.96 | 97.4, 98.0 | 0.98, 0.98 | 98.6, 98.5 |
| 4.51 | | | | 84 | 0.99, 0.99 | 100, 100 | 0.95, 0.97 | 96.9, 98.4 | 0.99, 0.99 | 98.7, 98.5 |

TABLE 14

Summary of 0.4 mg/ml, pH 5.0 AM424 Formulation Stability Following Storage at 8° C. and 25° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 5.02 | citrate | 0.4 | 8 | 0 | 0.38, 0.37 | 100, 100 | <u>0.36, 0.36</u> | 98.8, 98.7 | 0.38, 0.38 | 98.6, 98.4 |
| — | | | | 7 | <u>0.37, 0.37</u> | 100, 100 | 0.38, 0.38 | 98.4, 98.4 | <u>0.37, 0.37</u> | 98.1, 98.1 |
| 5.03 | | | | 13 | 0.37, 0.37 | 100, 100 | 0.38, 0.38 | 98.4, 98.4 | 0.38, 0.38 | 98.6, 98.7 |
| — | | | | 19 | 0.37, 0.37 | 100, 100 | 0.37, 0.37 | 98.4, 98.5 | <u>0.37, 0.37</u> | 98.3, 98.0 |

TABLE 14-continued

Summary of 0.4 mg/ml, pH 5.0 AM424 Formulation Stability Following Storage at 8° C. and 25° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 5.06 | | | | 27 | <u>0.38, 0.38</u> | 100, 100 | <u>0.38, 0.37</u> | 98.4, 98.5 | 0.38, 0.38 | 98.6, 98.6 |
| 5.04 | | | | 41 | 0.39, 0.39 | 100, 100 | 0.38, 0.37 | 97.8, 97.9 | 0.38, 0.38 | 98.7, 98.7 |
| 5.07 | | | | 55 | 0.39, 0.39 | 100, 100 | 0.37, 0.37 | 97.7, 97.5 | 0.39, 0.38 | 98.8, 98.7 |
| 5.02 | citrate | 0.4 | 25 | 0 | 0.38, 0.37 | 100, 100 | <u>0.36, 0.36</u> | 98.8, 98.7 | 0.38, 0.38 | 98.6, 98.4 |
| — | | | | 7 | 0.37, 0.37 | 100, 100 | <u>0.37, 0.36</u> | 97.0, 97.0 | <u>0.38, 0.38</u> | 98.7, 98.5 |
| 5.05 | | | | 13 | 0.38, 0.37 | 100, 100 | 0.36, 0.37 | 95.4, 95.1 | <u>0.37, 0.37</u> | 98.7, 98.7 |
| — | | | | 19 | 0.37, 0.37 | 100, 100 | 0.35, 0.35 | 93.8, 93.9 | 0.38, 0.38 | 98.8, 98.8 |
| 5.05 | | | | 27 | <u>0.38, 0.38</u> | 100, 100 | <u>0.34, 0.34</u> | 92.0, 91.8 | 0.39, 0.39 | 99.3, 99.0 |
| 5.06 | | | | 41 | 0.39, 0.39 | 100, 100 | 0.33, 0.34 | 87.0, 87.4 | 0.38, 0.38 | 99.1, 99.1 |
| 5.03 | | | | 55 | 0.39, 0.39 | 100, 100 | 0.30, 0.30 | 77.8, 77.9 | 0.39, 0.39 | 99.0, 98.9 |

Underlined values represent repeat analyses

TABLE 15

Summary of 0.4 mg/ml, pH 5.0 AM424 Formulation Stability Following Storage at −80° C. and −20° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.94 | citrate | 0.4 | −80 | 0 | 0.41, 0.40 | 100, 100 | 0.40, 0.40 | 98.9, 98.8 | 0.39, 0.39 | 98.8, 98.7 |
| 4.98 | | | | 28 | 0.41, 0.41 | 100, 100 | 0.39, 0.39 | 98.5, 98.5 | 0.39, 0.39 | 98.3, 98.3 |
| 4.98 | | | | 56 | 0.40, 0.40 | 100, 100 | 0.38, 0.38 | 98.6, 98.6 | 0.38, 0.38 | 98.4, 98.3 |
| 5.00 | | | | 84 | 0.42, 0.42 | 100, 100 | 0.40, 0.40 | 98.7, 98.4 | 0.41, 0.41 | 98.5, 98.5 |
| 4.94 | citrate | 0.4 | −20 | 0 | 0.41, 0.41 | 100, 100 | 0.40, 0.40 | 98.9, 98.8 | 0.39, 0.39 | 98.8, 98.7 |
| 4.95 | | | | 28 | 0.41, 0.41 | 100, 100 | 0.39, 0.39 | 98.5, 98.5 | 0.40, 0.39 | 98.5, 98.6 |
| 4.96 | | | | 56 | 0.40, 0.40 | 100, 100 | 0.38, 0.39 | 98.4, 98.6 | 0.39, 0.39 | 98.6, 98.6 |
| 4.97 | | | | 84 | 0.42, 0.42 | 100, 100 | 0.41, 0.41 | 98.6, 98.7 | 0.41, 0.41 | 99.0, 98.8 |

TABLE 16

Summary of 1.0 mg/ml, pH 5.0 AM424 Formulation Stability Following Storage at 8° C. and 25° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 5.00 | citrate | 1.0 | 8 | 0 | 0.98, 0.98 | 100, 100 | <u>0.95, 0.95</u> | 98.5, 98.5 | 0.97, 0.97 | 98.2, 98.1 |
| — | | | | 7 | <u>0.98, 0.98</u> | 100, 100 | <u>0.99, 0.99</u> | 98.5, 98.5 | <u>0.97, 0.98</u> | 98.5, 98.5 |
| 5.05 | | | | 13 | 0.97, 0.97 | 100, 100 | <u>0.94, 0.94</u> | 98.1, 98.2 | <u>0.96, 0.96</u> | 98.2, 98.0 |
| — | | | | 19 | 0.99, 0.99 | 100, 100 | 0.95, 0.95 | 98.1, 98.0 | 0.98, 0.98 | 98.5, 98.6 |
| 5.02 | | | | 27 | 0.98, 0.99 | 100, 100 | 0.99, 0.98 | 98.0, 98.1 | 0.98, 0.98 | 98.6, 98.6 |
| 5.04 | | | | 41 | 0.96, 0.96 | 100, 100 | 0.94, 0.94 | 97.5, 97.6 | 0.95, 0.96 | 98.7, 98.6 |
| 5.04 | | | | 55 | 0.98, 0.98 | 100, 100 | 0.94, 0.94 | 97.0, 97.2 | 0.97, 0.98 | 98.6, 98.8 |
| 5.00 | citrate | 1.0 | 25 | 0 | 0.98, 0.98 | 100, 100 | 0.95, 0.95 | 98.5, 98.5 | 0.97, 0.97 | 98.2, 98.1 |
| — | | | | 7 | <u>0.97, 0.97</u> | 100, 100 | <u>0.97, 0.97</u> | 97.0, 97.0 | <u>0.98, 0.98</u> | 98.8, 98.6 |
| 5.06 | | | | 13 | 0.98, 0.97 | 100, 100 | 0.92, 0.91 | 94.6, 94.7 | <u>0.97, 0.97</u> | 98.8, 98.8 |
| — | | | | 19 | 0.99, 1.00 | 100, 100 | 0.90, 0.89 | 92.2, 92.3 | 0.98, 0.98 | 98.8, 98.6 |
| 5.05 | | | | 27 | 0.99, 0.99 | 100, 100 | <u>0.91, 0.91</u> | 90.3, 90.3 | 0.99, 0.98 | 98.8, 98.8 |
| 5.06 | | | | 41 | 0.97, 0.97 | 100, 100 | 0.80, 0.80 | 83.0, 83.0 | 0.96, 0.96 | 98.6, 98.7 |
| 5.00 | | | | 55 | 0.99, 0.98 | 100, 100 | 0.76, 0.76 | 77.7, 78.0 | 0.99, 0.97 | 99.0, 98.7 |

Underlined values represent repeat analyses

TABLE 17

Summary of 1.0 mg/ml, pH 5.0 AM424 Formulation Stability Following Storage at −80° C. and −20° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.96 | citrate | 1.0 | −80 | 0 | 1.00, 1.00 | 100, 100 | 0.98, 0.99 | 98.8, 98.8 | 0.98, 0.98 | 98.1, 98.1 |
| 4.97 | | | | 28 | 1.00, 0.99 | 100, 100 | 0.96, 0.96 | 98.2, 98.1 | 0.98, 0.98 | 98.4, 98.4 |
| 4.95 | | | | 56 | 0.97, 0.97 | 100, 100 | 0.95, 0.95 | 98.4, 98.4 | 0.96, 0.96 | 98.5, 98.4 |

TABLE 17-continued

Summary of 1.0 mg/ml, pH 5.0 AM424 Formulation Stability Following Storage at −80° C. and −20° C.

| measured pH | buffer | Nominal AM424 Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 4.97 | | | | 84 | 0.99, 0.99 | 100, 100 | 0.96, 0.96 | 98.4, 98.5 | 0.97, 0.97 | 98.5, 98.5 |
| 4.96 | citrate | 1.0 | −20 | 0 | 1.00, 1.00 | 100, 100 | 0.98, 0.98 | 98.8, 98.8 | 0.98, 0.98 | 98.1, 98.1 |
| 4.96 | | | | 28 | 0.99, 1.00 | 100, 100 | 0.97, 0.97 | 98.3, 98.2 | 0.98, 0.98 | 98.5, 98.4 |
| 4.94 | | | | 56 | 0.98, 0.97 | 100, 100 | 0.95, 0.95 | 98.3, 98.3 | 0.97, 0.96 | 98.6, 98.5 |
| 4.96 | | | | 84 | 0.99, 0.99 | 100, 100 | 0.96, 0.96 | 98.4, 98.3 | 0.97, 0.96 | 98.5, 98.6 |

EXAMPLE 2

I. Analytical Methods

A. Reversed Phase (RP), Ion Exchange (IE) and Size Exclusion (SEC) Assays were conducted as described in Example 1.

II. Buffer Composition

All LIF samples were prepared by dilution of stock LIF solution containing 3.67 mg/ml LIF in 2 mM phosphate buffer, pH 6.42 to give the desired final LIF concentration (either 0.4 or 1.0 mg/ml) and composition of buffer components. The final composition of each solution contained 10 mM citrate buffer, 5% w/v sorbitol and 0.01% w/v Polysorbate 80. Samples differed in the final concentration of phosphate buffer (present from the original stock LIF solution) depending on the dilution factor. The 0.4 mg/ml LIF solutions contained 0.22 mM residual phosphate while the 1.0 mg/ml LIF solutions contained 0.54 mM residual phosphate. The composition of each buffer was as follows:

A. Citrate Buffer for 0.4 mg/ml LIF Formulations

Solution A:
11.22 mM sodium citrate dihydrate (Merck #1.06448)
5.61% w/v sorbitol (Sigma Chemicals #S1876)
0.0112% Polysorbate 80 (Sigma Chemicals #P1754)

Solution B:
11.22 mM citric acid monohydrate (Merck #1.00244)
5.61% w/v sorbitol (Sigma Chemicals #S1876)
0.0112% Polysorbate 80 (Sigma Chemicals #P1754)

Solutions A and B were mixed to give a final pH of 5.5. Formulations were prepared by combining 0.109 parts stock LIF solution and 0.891 parts buffer to give a final LIF concentration of 0.4 mg/ml, a final buffer concentration of 10 mM, a final sorbitol concentration of 5% w/v and a final Polysorbate 80 concentration of 0.01% w/v. The measured osmolality of the final 0.4 mg/ml LIF formulation was 317 mOsm/kg.

B. Citrate Buffer for 1.0 mg/ml LIF Formulations

Solution A:
13.75 mM sodium citrate (Merck #1.06448)
6.88% w/v sorbitol (Sigma Chemicals #S1876)
0.0138% w/v Polysorbate 80 (Sigma Chemicals #P1754)

Solution B:
13.75 mM citric acid (Merck #1.00244)
6.88% w/v sorbitol (Sigma Chemicals S1876)
0.0138% w/v Polysorbate 80 (Sigma Chemicals P1754)

Solutions A and B were mixed to give a final pH of 5.5. Formulations were prepared by combining 0.272 parts stock LIF solution and 0.728 parts buffer to give a final LIF concentration of 1.0 mg/ml, a final buffer concentration of 10 mM, a final sorbitol concentration of 5% w/v and a final Polysorbate 80 concentration of 0.01% w/v. The measured osmolality of the final 1.0 mg/ml LIF formulation was 322 mOsm/kg.

II. Long Term Stability at 8° C. and 25° C.

A. Preparation of Samples for Storage at 8° C. and 25° C.

LIF formulations were prepared by dilution of stock LIF (3.67 mg/ml in 2 mM phosphate buffer, pH 6.42) with citrate buffer containing sorbitol and polysorbate 80 to give a final LIF concentration of 0.4 mg/ml or 1.0 mg/ml, a final buffer concentration of 10 mM, a final sorbitol concentration of 5% w/v and a final polysorbate 80 concentration of 0.01% w/v (see Section II). The theoretical pH was 5.5 and the actual pH of each sample was measured and recorded.

Under aseptic conditions in a laminar flow cabinet, the formulations were sterile filtered using 0.22 μm Millex GV (Millipore) filters. The first 1.15 ml of each filtrate was set aside and the vial marked accordingly. The remaining volume was filtered into a sterile 50 ml polypropylene tube. Aliquots of each formulation (1.15 ml/vial) were transferred using a multiple dispensing Eppendorf pipette with sterile tips into heat sterilised 2 ml glass vials and capped with sterile teflon lined rubber caps which were then crimped. Vials were labelled and duplicate vials of each formulation were retained for the initial analysis. The remaining vials were stored at either 8° C. or 25° C.

B. Sample Analysis

All LIF samples were analysed undiluted along with standards according to the methods described in Example 1. At each time point, 2 vials were withdrawn from the incubators and approximately 200 μl was removed from each using a sterile 1 ml syringe and a sterile needle. These aliquots were placed into polypropylene autosampler vials and sealed with caps containing self-sealing septa to allow repeat injections from the same vial without evaporation. The original glass sample vials were then marked with the time point and placed at −80° C. for repeat analysis (if required) or use in other studies.

Autosampler vials were transferred to the autosampler where they were maintained at 4° C. throughout the three analytical runs. The same sample and standard autosampler vials were used for each of the three analyses with the RP (10 μl injection volume) being conducted first, followed by the IEC (100 μl injection volume) and then the SEC (10 μl injection volume). The complete RP run took approximately 20 hours, and the IEC and SEC runs took approximately 15 hours each. It was assumed that any further degradation over this storage time in the autosampler would be minimal (standard solutions at pH 6.42 stored under the same conditions showed no change over the complete analytical period).

Selected samples were also analysed for particulates using a Malvern Instruments Zetasizer 3000 particle size instrument. Samples were withdrawn from the storage vials using a syringe and placed in the sample cuvette. Samples were counted for 120 sec using a 200 μm pinhole (to obtain the maximum signal), 90° scattering angle, and scattering source at 633 nm using a 10 mW He—Ne ion laser.

IV. Results

Data pertaining to solution pH, LIF concentration in mg/ml (determined by comparison to LIF standard solutions), and the area % for the main peak relative to the total peak area for all LIF related peaks in the chromatogram analysed using the three chromatographic methods are shown in Tables 18 and 19. For each set of samples, there was a slight decrease in solution pH of approximately 0.1 unit over the 92 day storage period.

1. Ion Exchange

A single main product (eluting at approximately 9 min) was seen in all samples stored at 8 and 25°. There was evidence of several minor degradation products in the ion exchange chromatograms, however, due to inadequate resolution between the different products, the exact number of products could not be determined. Samples prepared at pH 5.0 (initial study) and those at pH 5.5 (this study) stored at 8° C. and 25° C. for 8 weeks were compared. The chromatograms were normalised with respect to the retention time for the main peak to take into account slight changes in the chromatography between the two studies. In each case, the product distribution was similar with a higher proportion of the main degradation product noted in the pH 5.5 samples relative to the pH 5.0 samples.

The IEC results for the samples, wherein the main LIF peak was plotted as a percentage of the total area for all LIF related peaks in the chromatogram as a function of storage time illustrated the dependence of LIF stability on temperature. The relative stability under each storage condition was similar for the 0.4 and 1.0 mg/ml formulations. After 92 days storage at 8° C., 95–96% of the total peak area was present as the main LIF peak. Following storage at 25° C. for 92 days, this value was reduced to approximately 56–58%.

The IEC stability data (main peak area expressed as a percentage of the total) obtained for samples at pH 5.5 and that from the previous study with samples prepared at pH 5.0 were compared. At 25° C., a slight increase in the rate of degradation was evident at pH 5.5.

2. Reversed Phase

RP chromatograms for the samples all displayed essentially the same elution characteristics. In all cases, the chromatograms showed the presence of only one main peak eluting at approximately 36 min.

The RP results wherein the measured concentration was plotted as a function of storage time illustrated the absence of significant change in the measured concentration over the storage period.

3. Size Exclusion

SEC chroratograms for the samples displayed essentially the same elution characteristics. In all cases, the chromatograms showed the presence of one main peak eluting at approximately 25 min and a minor peak eluting at approximately 21 min.

The SEC results wherein the measured concentration was plotted as a function of storage time illustrated the absence of significant change in the measured concentration over the storage period. Using the SEC method, there was no evidence of chain cleavage or crosslinking under the storage conditions studied.

4. Particle Size Analysis

Samples stored for 102 days at 8 and 25° C. were analysed for particulates using a laser light scattering instrument. AU of the samples analysed displayed a count rate of "0–0.5 kCps" which effectively means that the samples contained no particulates (i.e. no signal was measurable).

V. Summary

These studies demonstrated that formulations prepared at pH 5.5 were stable for up to 13 weeks when stored at 8° C. with loss of the parent compound being approximately 3% as shown by IEC. After storage for 56 days at 8° C., the loss of LIF was approximately 2% in comparison to approximately 1% for pH 5.0 samples stored under the same conditions (data from the initial study). At 25° C., the rate of degradation at pH 5.5 was significantly increased with approximately 12% loss occurring in 4 weeks. In comparison, pH 5.0 samples showed a decrease in LIF concentration of approximately 7–9% after 4 weeks at 25° C. As in the initial study, no loss of LIF was detected by RP or SEC under any of the conditions studied.

TABLE 18

Summary of AM424 Stability for 0.4 mg/ml Formulations at pH 5.5 Following Storage at 8° C. and 25° C.

| Measured pH | buffer | Nominal LIF Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc. (mg/ml) | SEC - Main Peak (area %) |
|---|---|---|---|---|---|---|---|---|---|---|
| 5.61 | citrate | 0.4 | 8 | 0 | 0.42, 0.44 | 100, 100 | 0.40, 0.40 | 98.6, 98.6 | 0.40, 0.40 | 98.7, 98.7 |
| 5.56 | | | | 14 | 0.38, 0.38 | 100, 100 | 0.37, 0.37 | 97.9, 98.0 | 0.39, 0.39 | 98.7, 98.7 |
| 5.59 | | | | 29 | 0.41, 0.41 | 100, 100 | 0.39, 0.39 | 98.4, 98.3 | 0.41, 0.41 | 98.8, 98.7 |
| 5.51 | | | | 42 | 0.40, 0.41 | 100, 100 | 0.37, 0.38 | 98.1, 98.7 | 0.40, 0.39 | 98.6, 98.7 |
| 5.47 | | | | 56 | 0.39, 0.39 | 100, 100 | 0.39, 0.39 | 97.3, 97.1 | 0.40, 0.40 | 98.6, 98.7 |
| 5.48 | | | | 77 | 0.39, 0.40 | 100, 100 | 0.38, 0.38 | 96.2, 96.3 | 0.39, 0.39 | 98.9, 98.9 |
| 5.48 | | | | 92 | 0.42, 0.40 | 100, 100 | 0.37, 0.37 | 95.7, 95.8 | 0.38, 0.38 | 98.6, 98.7 |
| 5.61 | citrate | 0.4 | 25 | 0 | 0.42, 0.44 | 100, 100 | 0.40, 0.40 | 98.6, 98.6 | 0.40, 0.40 | 98.7, 98.7 |
| 5.57 | | | | 14 | 0.38, 0.39 | 100, 100 | 0.35, 0.35 | 92.8, 92.8 | 0.39, 0.39 | 98.8, 98.9 |
| 5.59 | | | | 29 | 0.41, 0.42 | 100, 100 | 0.35, 0.35 | 86.9, 86.8 | 0.41, 0.41 | 98.9, 99.0 |
| 5.52 | | | | 42 | 0.41, 0.41 | 100, 100 | 0.31, 0.32 | 81.0, 81.8 | 0.38, 0.40 | 98.8, 99.0 |
| 5.48 | | | | 56 | 0.39, 0.39 | 100, 100 | 0.29, 0.29 | 71.6, 71.9 | 0.41, 0.40 | 99.2, 99.0 |
| 5.48 | | | | 77 | 0.41, 0.40 | 100, 100 | 0.26, 0.26 | 63.8, 64.0 | 0.40, 0.39 | 99.3, 99.1 |
| 5.48 | | | | 92 | 0.40, 0.42 | 100, 100 | 0.23, 0.23 | 57.4, 57.7 | 0.39, 0.40 | 98.9, 99.2 |

TABLE 19

Summary of AM424 Stability for 1.0 mg/ml Formulations at pH 5.5 Following Storage at 8° C. and 25° C.

| Measured pH | buffer | Nominal LIF Conc. (mg/ml) | Storage Temp. (C.) | Storage Time (days) | RP - Measured Conc. (mg/ml) | RP - Main Peak (area %) | IEC - Measured Conc. (mg/ml) | IEC - Main Peak (area %) | SEC - Measured Conc (mg/ml) | SEC - Main Peak (area %) |
|---|---|---|---|---|---|---|---|---|---|---|
| 5.61 | citrate | 1.0 | 8 | 0 | 1.09, 1.08 | 100, 100 | 1.00, 1.00 | 98.6, 98.6 | 1.01, 1.01 | 98.6, 98.6 |
| 5.58 | | | | 14 | 0.98, 0.99 | 100, 100 | 0.96, 0.96 | 97.7, 97.7 | 0.99, 0.99 | 98.6, 98.7 |
| 5.61 | | | | 29 | 1.01, 1.02 | 100, 100 | 0.99, 0.99 | 97.5, 97.6 | 1.01, 1.01 | 98.5, 98.5 |
| 5.57 | | | | 42 | 1.00, 1.01 | 100, 100 | 0.97, 0.97 | 97.3, 97.2 | 0.99, 0.98 | 98.4, 98.6 |
| 5.54 | | | | 56 | 1.00, 0.99 | 100, 100 | 0.96, 0.96 | 96.8, 96.6 | 1.02, 1.02 | 98.4, 98.5 |
| 5.52 | | | | 77 | 1.03, 1.02 | 100, 100 | 0.94, 0.94 | 96.0, 95.9 | 0.98, 0.99 | 98.5, 98.5 |
| 5.52 | | | | 92 | 1.06, 1.04 | 100, 100 | 0.95, 0.94 | 95.3, 95.3 | 0.98, 0.98 | 98.4, 98.4 |
| 5.61 | citrate | 1.0 | 25 | 0 | 1.09, 1.08 | 100, 100 | 1.00, 1.00 | 98.6, 98.6 | 1.01, 1.01 | 98.6, 98.6 |
| 5.58 | | | | 14 | 0.98, 0.98 | 100, 100 | 0.90, 0.90 | 91.7, 91.8 | 0.99, 0.99 | 98.7, 98.7 |
| 5.62 | | | | 29 | 1.02, 1.01 | 100, 100 | 0.87, 0.87 | 85.6, 85.7 | 1.02, 1.02 | 98.7, 98.7 |
| 5.59 | | | | 42 | 1.02, 1.01 | 100, 100 | 0.80, 0.80 | 80.0, 79.8 | 0.98, 0.98 | 98.8, 98.8 |
| 5.54 | | | | 56 | 0.99, 1.02 | 100, 100 | 0.71, 0.71 | 68.9, 69.2 | 1.02, 1.03 | 98.8, 98.7 |
| 5.53 | | | | 77 | 1.02, 1.03 | 100, 100 | 0.64, 0.64 | 61.0, 61.6 | 0.98, 0.98 | 98.9, 98.8 |
| 5.52 | | | | 92 | 1.04, 1.09 | 100, 100 | 0.59, 0.58 | 56.0, 56.1 | 0.99, 0.99 | 98.8, 98.7 |

EXAMPLE 3

I. Sample Preparation

8° C. and 25° C. LIF Samples

LIF formulations were prepared by a dilution of stock LIF (3.67 mg/ml in 2 mM phosphate buffer) with citrate buffer containing sorbitol or NaCl to give a final LIF concentration of 0.4 mg/ml, a final buffer concentration of 10 mM, a final sorbitol concentration of 5% w/v or a final NaCl concentration of 0.9% w/v. The theoretical pH was 5.0 in all cases. Formulations were prepared and filled into vials as described previously.

II. Analytical Methods

Samples and standards were prepared as previously described. Analyses were conducted by RP and SEC and IEC was conducted using the Polycat A column.

The RP and SEC assays were the same as those described in Example 1. The IEC assay was conducted using a PolyLC PolyCAT A cation exchange column, pH 6 phosphate buffer and a salt gradient. Detection was at 215 nm.

III. Results

Ion Exchange

IEC data for 0.4 mg/ml formulations are shown in Tables 20 and 21. The results expressed as a percentage of the initial concentration remaining after the storage period indicated that the most stable formulations were the pH 5.0 citrate buffer containing sorbitol and Tween 80 and the pH 5.0 citrate buffer containing NaCl.

SEC

SEC data for 0.05 and 0.4 mg/ml formulations are plotted with the main peak expressed as a % of the total area. There was some variability in the 0.05 mg/ml samples most likely due to the low concentration. There were no real trends for either buffer at 8° C. or 25° C.

Freeze-Thaw Cycling

Freeze-thaw cycling studies for pH 5 citrate buffers containing sorbitol or NaCl were analysed by SEC. After the 5th cycle there was a trend toward a decrease in the main peak as a % of the total area and a slight increase in the pre-eluting high molecular weight peak.

TABLE 20

Stability of 0.4 mg/mL LIF formulations following storage at 8° C. measured by IEC.

| Storage Time (Weeks) | Citrate/Sorbitol/Tween pH 5.0 (% of initial conc remaining) | Citrate/Sorbitol/Tween pH 5.5 (% of initial conc remaining) | Citrate/Sorbitol pH 5.0 (% of initial conc remaining) | Citrate/NaCl pH 5.0 (% of initial conc remaining) |
|---|---|---|---|---|
| 0 | 100 | 100 | 100 | 100 |
| 2 | 99.7 | 99.4 | 99.9 | 101.6 |
| 4 | 99.8 | 99.7 | 99.7 | 101.1 |
| 6 | 99.2 | 99.2 | 98.2 | 98.8 |
| 8 | 98.8 | 98.5 | 97.0 | 98.2 |

TABLE 21

Stability of 0.4 mg/Ml LIF formulations following storage at 25° C. measured by IEC.

| Storage Time (Weeks) | Citrate/Sorbitol/Tween pH 5.0 (% of initial conc remaining) | Citrate/Sorbitol/Tween pH 5.5 (% of initial conc remaining) | Citrate/Sorbitol pH 5.0 (% of initial conc remaining) | Citrate/NaCl pH 5.0 (% of initial conc remaining) |
|---|---|---|---|---|
| 0 | 100 | 100 | 100 | 100 |
| 2 | 96.4 | 94.1 | 84.0 | 91.8 |
| 4 | 93.0 | 88.0 | 80.6 | 86.2 |

TABLE 21-continued

Stability of 0.4 mg/Ml LIF formulations following storage at 25° C. measured by IEC.

| Storage Time (Weeks) | Citrate/Sorbitol/Tween pH 5.0 (% of initial conc remaining) | Citrate/Sorbitol/Tween pH 5.5 (% of initial conc remaining) | Citrate/Sorbitol pH 5.0 (% of initial conc remaining) | Citrate/NaCl pH 5.0 (% of initial conc remaining) |
|---|---|---|---|---|
| 6 | 88.6 | 83.0 | 72.2 | 81.5 |
| 8 | 78.9 | 72.9 | 68.7 | 76.0 |

EXAMPLE 4

Preferred compositions comprise:
LIF in a concentration of 400 to 1000 mg/ml
pH of about 4.0–6.0
surfactant
isotonicity agent
buffer.
Particularly preferred compositions are those wherein the pH range is about 4.5–5.5.

EXAMPLE 5

A particularly preferred composition comprises:
LIF in a concentration of 400 to 1000 mg/mil
pH of about 5.0
5% w/w sorbitol
0.01% polysorbate 80
citrate or acetate buffer.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. A composition comprising leukaemia inhibitory factor (LIF) and a stabilizing agent, additives for maintaining pH and isotonicity and one or more pharmaceutically acceptable carriers wherein the pH of the composition is between about 3.5 and 6.5.

2. A composition according to claim 1 wherein the stabilizing agent is an agent which increases or maintains the conformational stability of LIF.

3. A composition according to claim 2 wherein the stabilizing agent is selected from a polyhydric alcohol, a pharmaceutically acceptable salt, a buffer species, a sugar and a pharmaceutically acceptable polymeric compound.

4. A composition according to claim 3 wherein the polyhydric alcohol is sorbitol.

5. A composition according to claim 2 wherein the stabilizing agent is an anionic, cationic, amphoteric or nonionic surfactant.

6. A composition according to claim 5 wherein the surfactant is selected from a fatty alcohol, a glyceryl ester and a fatty acid ester of a fatty alcohol or other alcohol.

7. A composition according to claim 2 wherein the stabilizing agent is selected from a polysorbate, a polyoxyethylene derivative and a pharmaceutically acceptable polyoxyethylene-polyoxpropylene copolymer.

8. A composition according to claim 3 wherein the buffer species is selected from a phosphate, citrate and acetate buffer.

9. A composition according to claim 8 wherein the buffer species is a citrate or acetate buffer.

10. A composition comprising leukaemia inhibitory factor (LIF), additives for maintaining pH and isotonicity and one or more pharmaceutically acceptable carriers and/or diluents and wherein the composition has a pH of between about 3.5 and 6.5.

11. A composition according to claim 10 wherein the aggregation of LIF is reduced over time.

12. A composition according to claim 1 wherein LIF is present in an amount from about 0.1 µg/ml to about 100 mg/ml.

13. A composition according to claim 9 wherein LIF is present in an amount from about 0.1 µg/ml to about 100 mg/ml.

14. A composition according to claim 1 wherein the pH of the composition is between about 4.5 and 6.5.

15. A composition according to claim 14 wherein the pH of the composition is between about 4.5 and 6.0.

16. A composition according to claim 2 wherein the stabilizing agent is a surfactant.

17. A composition according to claim 5 wherein the stabilizing agent is polysorbate 20 and/or polysorbate 80.

18. A composition according to claim 10 wherein the composition has a pH of between about 4.5 and 6.5.

19. A composition according to claim 18 wherein the composition has a pH of between about 4.5 and 6.0.

20. A composition according to any one of claims 1, 14 or 15 wherein the stabilizing agent facilitates reduced aggregation of LIF.

21. A composition according to any one of claims 1, 14 or 15 wherein the stabilizing agent facilitates a reduction in the deamidation of LIF.

22. A composition according to any one of claims 10, 18 or 19 wherein the deamidation of LIF is reduced over time.

23. A composition according to any one of claims 10, 18 or 19 where the pH is maintained by the presence of a buffer species selected from a phosphate, citrate and acetate buffer.

24. A composition according to claim 23 wherein the buffer species is a citrate or acetate buffer.

25. A method for preparing a composition comprising leukaemia inhibitory factor (LIF) wherein said composition exhibits reduced deamidation and/or aggregation of LIF over times said method comprising admixing LIF with a stabilizing agent and additives for maintaining pH and isotonicity.

26. A method according to claim 25 wherein the stabilizing agent is an agent which increases or maintains the conformational stability of LIF or is a surfactant.

27. A method according to claim 26 wherein the stabilizing agent is selected from a polyhydric alcohol, a pharmaceutically acceptable salt, a buffer species, a sugar and a pharmaceutically acceptable polymeric compound.

28. A method according to claim 27 wherein the polyhydric alcohol is sorbitol.

29. A method according to claim 26 wherein the surfactant is an anionic, cationic, amphoteric or non-ionic surfactant.

30. A method according to claim 29 wherein the surfactant is selected from a fatty alcohol, glyceryl ester and a fatty acid ester of a fatty alcohol or other alcohol.

31. A method according to claim 25 wherein the additives for maintaining pH and isotonicty are selected from a phosphate, citrate and acetate buffer.

32. A method according to claim 31 wherein the additives for maintaining pH and isotonicity are citrate or acetate buffer.

33. A method according to claim 25 further comprising adjusting the pH to between about 3.5 and about 6.5.

34. A method according to claim 25 further comprising admixing at least one of a pharmaceutically acceptable carrier or diluent.

35. A method according to claim 27 wherein the stabilizing agent is selected from a polysorbate, a polyoxyethylene derivative and a pharmaceutically acceptable polyoxyethylene-polyoxypropylene copolymer.

36. A method according to claim 35 wherein the polysorbate is polysorbate 20 and/or polysorbate 80.

37. A method according to claim 33 further comprising adjusting the pH to between about 4.5 and about 6.5.

38. A method according to claim 33 further comprising adjusting the pH to between about 4.5 and 6.0.

39. A method of preparing a composition comprising leukemia inhibitory factor (LIF) wherein said composition exhibits improved chemical or physical stability of LIF, said method comprising admixing LIF or its derivative or homologue with a stabilizing agent.

40. A method according to claim 39 wherein the stabilizing agent is selected from a polyhydric alcohol, a pharmaceutically acceptable salt, a buffer species, a sugar and a pharmaceutically acceptable polymeric compound.

41. A method according to claim 40 wherein the polyhydric alcohol is sorbitol.

42. A method according to claim 40 wherein the stabilizing agent is an anionic, cationic, amphoteric or non-ionic surfactant.

43. A method according to claim 42 wherein the surfactant is selected from a fatty alcohol, glyceryl ester and a fatty acid ester of a fatty alcohol or other alcohol.

44. A method according to claim 39 where the stabilizing agent is selected from a polysorbate, a polyoxyethylene derivative or a pharmaceutically acceptable polyoxyethylene-polyoxypropylene copolymer.

45. A method according to claim 40 wherein the buffer species is selected from a phosphate, citrate and acetate buffer.

46. A method according to claim 45 wherein the buffer species is a citrate or acetate buffer.

47. A method according to claim 39 where the pH of the composition is between about 3.5 to about 6.5.

48. A method according to claim 47 wherein the pH is between about 4.5 and about 5.5.

49. A method according to claim 48 wherein the pH is between about 4.5 and about 6.0.

* * * * *